(12) United States Patent
Wilson et al.

(10) Patent No.: US 6,814,845 B2
(45) Date of Patent: Nov. 9, 2004

(54) METHOD FOR DEPOSITING AN ENZYME ON AN ELECTRICALLY CONDUCTIVE SUBSTRATE

(75) Inventors: George S. Wilson, Lawrence, KS (US); Xiaohong Chen, Lawrence, KS (US); Norio Matsumoto, Matsudo Chiba (JP); Yibai Hu, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 11 days.

(21) Appl. No.: 09/990,514

(22) Filed: Nov. 21, 2001

(65) Prior Publication Data

US 2003/0104119 A1 Jun. 5, 2003

(51) Int. Cl.$^7$ .............................. C25D 13/04; C25D 9/04
(52) U.S. Cl. ........................ 204/486; 204/489; 204/507; 205/106; 205/149; 205/198; 205/317; 435/176; 435/817
(58) Field of Search .................................. 204/486, 489, 204/507; 205/106, 149, 198, 317; 435/176, 817

(56) References Cited

U.S. PATENT DOCUMENTS

| | | |
|---|---|---|
| 4,721,677 A | 1/1988 | Clark, Jr. |
| 5,165,407 A | 11/1992 | Wilson et al. |
| 5,166,063 A | 11/1992 | Johnson |
| 5,286,364 A | 2/1994 | Yacynych et al. |
| 5,310,469 A | 5/1994 | Cunningham et al. |
| 5,411,647 A | 5/1995 | Johnson et al. |
| 5,540,828 A | 7/1996 | Yacynych |
| 6,242,235 B1 * | 6/2001 | Shultz et al. .................. 435/194 |
| 6,340,421 B1 * | 1/2002 | Vachon et al. ............... 205/133 |
| 6,342,346 B1 * | 1/2002 | Raguse et al. .................. 435/4 |
| 6,482,517 B1 * | 11/2002 | Anderson ............... 428/402.24 |

OTHER PUBLICATIONS

Chiarotto et al.; Electropolymerization of Hydroxybenzene and Aminobenzene Isomers on Platinum Electrodes to Assemble Interference–Free Electrochemical Biosensors; *Electrochemica Acta.*, vol. 41, No. 11/12, pp. 1793–1800 (1996).

Strike et al.; Electrochemical Techniques for the Modification of Microelectrodes; *Biosensors & Bioelectronics*, 10:61–66 (1995).

Arrigan et al.; A Scanning Force Microscopy Study of Poly(phenol) Films Containing Immobilized Glucose Oxidase; *Biosensors & Bioelectronics*, 13:293–304 (1998).

(List continued on next page.)

*Primary Examiner*—Roy King
*Assistant Examiner*—William T. Leader
(74) *Attorney, Agent, or Firm*—Stinson Morrison Hecker, LLP

(57) ABSTRACT

Improved biosensors are provided having excellent selectivity and stability properties, together with methods of preparing the biosensors. A preferred biosensor includes an electrode (12) having enzyme (16) deposited thereon together with a layer of electropolymerized polymer (18) intermingled with the enzyme (16); a crosslinked silane film (20) is applied over the polymer layer (18), and a final coating (22) of polyurethane is formed over the film (20). In preparative procedures, the enzyme (16) is electrodeposited using an aqueous enzyme solution containing a nonionic surfactant at a concentration level preferably in excess of the critical micelle concentration of the surfactant. In the case of a glucose sensor, the polymer layer (18) is preferably polyphenol, while the silane film is crosslinked (3-aminopropyl) trimethoxysilane. The preferred biosensors have greatly enhanced selectivity stabilities.

37 Claims, 18 Drawing Sheets

Conc. of Triton X-100 (mM)

OTHER PUBLICATIONS

Im et al.; Electrodeposited GOD/BSA Electrodes: Ellipsometric Study and Glucose–Sensing Behaviour; *Sensors and Actuators*, B 24–25 (1995) 149–155.

Warriner et al.; The Modification of Enzyme Electrode Properties with Non–Conducting Electropolymerised Films; *Biosensors & Bioelectronics*, 10:831–839 (1995).

Guerrieri et al.; Electrosynthesized Non–Conducting Polymers as Permselective Membranes in Amperometric Enzyme Electrodes; *Biosensors & Bioelectronics*; 13(1): 103–112 (1998).

Yu et al.; An Independently Addressable Microbiosensor Array: What are the limits of sensing element density; *Faraday Discuss.*, 2000, 116, 305–317.

Johnson et al.; Reproductive Electrodeposition Technique for Immobilizing Glucose Oxidase; ACS Symp. Ser. (1994) 556; Diagnostic Biosensor Polymers.

Geise et al. Electropolymerized Films to Prevent Interferences and Electrode Fouling in Biosensors; *Biosensors & Bioelectronics*, 6:151–160 (1991).

\* cited by examiner

Fig. 10A 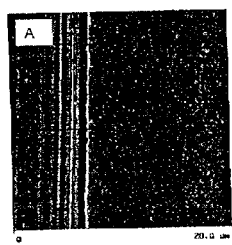 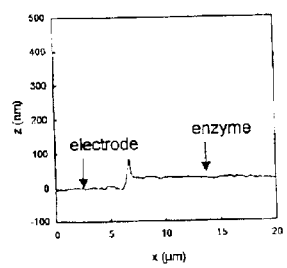 Fig. 10C
Fig. 10B 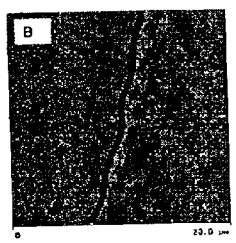 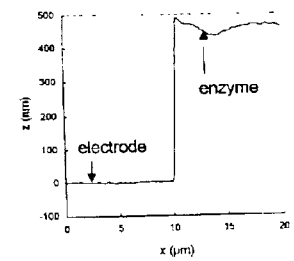 Fig. 10D

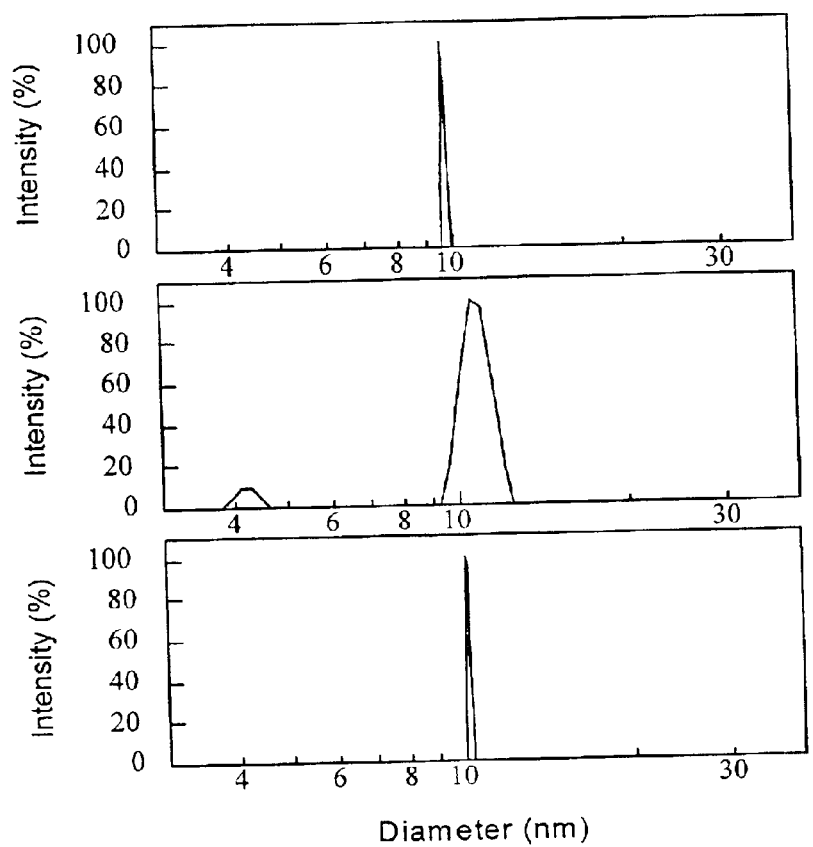

METHOD FOR DEPOSITING AN ENZYME ON AN ELECTRICALLY CONDUCTIVE SUBSTRATE

BACKGROUND OF THE INVENTION

1. Field of the Invention

The present invention is broadly concerned with improved implantable biosensors and methods of production thereof. More particularly, the invention pertains to biosensors having enhanced sensitivity and stability characteristics coupled with relative ease of manufacture. The biosensors are preferably fabricated using enzymes, and especially oxidase enzymes such as glucose oxidase.

2. Description of the Prior Art

The enzyme electrode, and especially the glucose electroenzymatic biosensor, has served for more than 25 years as a valuable clinical tool for detecting and monitoring diabetes. A majority of glucose sensors, especially those used in in-vivo applications, are based on the rate of glucose oxidase-catalyzed oxidation of glucose by dioxygen, where the rate of the reaction is measured by monitoring the formation of hydrogen peroxide or the consumption of oxygen. The fabrication of such a sensor involves the controlled deposition of a permselective polymer layer used to eliminate interferences such as ascorbate, urate and acetaminophen, an enzyme layer, and an outer layer that renders the sensor response mass transfer rather than kinetically controlled and which also provides a biocompatible interface with the surrounding environment. The use of thick film techniques, including screen printing, has been demonstrated to be successful in the preparation of sensors with reasonably reproducible characteristics, and this approach has been applied, for example, in the electrochemically-based sensors used for self-monitoring of blood glucose as marketed by Abbott Laboratories (Medisense) and others. If, however, it is desired to employ a cylindrical geometry or to prepare a sensor array, then the reproducible deposition of the various functional layers becomes significantly more complicated. Thus it would be of considerable advantage to control the preparation of the sensor electrochemically, especially when the sensing elements in an array are themselves electrochemically addressable. This would also allow for the deposition of different enzymes in various parts of the array.

Electropolymerization makes it possible to generate a coating on small electrodes of complex geometry and to do so precisely in one or two rapid and simple steps. In general, electrochemically-mediated fabrication of biosensors has been accomplished in two ways. First, a polymer layer is formed directly on the electrode, and polymers formed from such monomers as pyrrole, aniline, tyramine, o-aminophenol and o-phenylenediamine have been used to create a permselective layer before or after the application of enzyme solution and cross-linking with glutaraldehyde. A second approach involves the entrapment of enzyme in a growing polymer network by co-polymerization of enzyme and monomer. In some cases a monomer unit is attached to the enzyme to facilitate this process. Yacynych employed a copolymer of 1,3-diaminobenzene and resorcinol as the preferred film for blocking interferences from the surface of carbon or partially platinized carbon electrodes (Geise, R. J.; et al., *Biosens. Bioelectron.*, 1991, 6, 151–160). Vadgama and coworkers found that electropolymerized 4-aminophenol and then phenol constituted an exceptionally selective film against acetaminophen and ascorbate in glucose biosensors (Eddy, S.; et al., *Biosens. Bioelectron.*, 1995, 10, 831–839). Curulli et al (Carelli, I.; et al., *Electrochim. Acta*, 1996, 41, 1793–1800 reported the results that poly(1,3-diaminobenzene/catechol) was the most efficient polymer to prevent the interference of acetaminophen. It has also been pointed out that electropolymerized films have significantly different characteristics when formed on different electrode materials and under different electropolymerization conditions. Experience has shown that these approaches typically give sensors of moderate activity but often high selectivity, but that both of these essential characteristics deteriorate quickly over a period of several days. The fact that the diffusion of enzyme and monomer cannot proceed at the same rate makes it difficult to enrich the composite layer with enzyme without at the same time degrading the permselective properties of the polymer.

U.S. Pat. Nos. 5,540,828, 5,286,364, 5,165,407, 5,310,469, 5,411,647, 5,166,063 and 4,721,677 describe various types of electrochemical biosensors.

SUMMARY OF THE INVENTION

The present invention overcomes many of the problems outlined above and provides biosensors such as implantable glucose sensors which can be economically prepared and which have excellent selectivity and stability characteristics far in excess of typical prior art sensors. Selectivity, or the ability to exclude electroactive interferants, is defined as, in the case of a glucose sensor, the percent change in the electrical signal at 5 mM glucose according to the relationship % Interf=$((I_{Tot}-I_{Glu})/I_{Glu})\times100$, where $I_{Glu}$ is the current response for glucose and $I_{Tot}$ is the current response of the glucose and interferant. Current response is defined as the current produced by the sensor in response to the analyte. The current response produced by the sensor in response to the analyte divided by the analyte concentration is herein referred to as the sensor sensitivity. For a biosensor prepared in accordance with this invention, the ratio of the current response at 5 mM glucose to that for 0.1 mM acetaminophen should be no less than about 100 in vitro.

Broadly speaking, a method of preparing a biosensor in accordance with the invention includes providing an electrically conductive biosensor electrode, which is immersed with a reference electrode in an aqueous conductive dispersion containing an enzyme and a non-ionic surfactant, the latter being present in an amount at least equal to the critical micelle concentration for the surfactant in the dispersion. A potential is then applied across the electrodes, causing the enzyme to deposit on the biosensor electrode. Next, the enzyme-deposited biosensor electrode is immersed in synthetic monomer and an electropolymerization procedure is carried out to create a polymer layer on the electrode which is intermingled with the initially deposited enzyme. In preferred forms, the electrode is next coated with a silane and then a polyurethane to complete the biosensor.

In more detail, the biosensor electrode (or more broadly an electrically conductive substrate) is typically formed of a metal alloy such as Pt—Ir or other noble metal; however, other conductive electrodes such as graphite electrodes can also be used. Normally, the electrode is in the form of a thin wire (having a diameter of from about 0.01 to 0.3 millimeters), and may have insulation over the majority of the length of the wire, leaving only a small stripped section to serve as an enzyme-receiving zone.

Virtually any enzyme can be deposited on the biosensor electrode, depending upon the nature of the analyte to be detected. The most useful enzymes are the oxidase enzymes, such as those selected from the group consisting of glucose, lactate, oxalate, D-aspartate, L-amino acid, D-amino acid, galactose, sarcosine, urate, ethanol, lysine, glutamate, cholesterol, glycerol, pyruvate, choline, ascorbate, and monoamine oxidases. Of these, the glucose, lactate, pyruvate, glutamate, cholesterol and choline oxidase enzymes are the most important.

During the initial deposition of the enzyme, it is preferred to employ an aqueous dispersion (normally a solution) which is buffered to a pH of about 7–8, more preferably about 7, containing the enzyme and a compatible surfactant (i.e., a surfactant which will facilitate enzyme deposition and not otherwise interfere with the desired electrodeposition). A variety of surfactants can be used in this context, although the nonionic surfactants are most preferred. One class of surfactants has been found to be particularly useful, namely the Triton surfactants, which are octylphenol ethoxylates, produced by the polymerization of octylphenol with ethylene oxide. A preferred surfactant is Triton X-100 which may be obtained from Sigma-Aldrich, Corp. (St. Louis, Mo.). The Triton X-100 product information sheet distributed by Sigma-Aldrich, Corp. is incorporated by reference herein. Triton X-100 comprises between about 9–10 moles of ethylene oxide per mole of octylphenol. Other surfactants of interest include nonylphenol ethoxylates, alkyl glucosides, alkyl maltosides, glucamides, alkyl polyoxyethylenes, alkyl glucopyranosides, alkyl thio-glucopyranosides, alkyl maltopyranosides, alkyl thio-maltoppyranosides, alkyl galacto-pyranosides, alkyl sucroses, glucamides, hyrdroxyethylglucamides, phenyl polyoxyethylenes, dimethylamine-N-oxides, cholate derivatives, n-octyl hydroxyalkylsulphoxides, sulphobetaines, and phosphocholine compounds.

An important feature of the enzyme deposition dispersion is that it contains the selected surfactant at a concentration of at least about the critical micelle concentration thereof, and more preferably a concentration within the range of from about the critical micelle concentration up to about 10 times the critical micelle concentration. Also, the relative amounts of surfactant and enzyme should be maintained. Generally, the molar ratio of the enzyme to the surfactant in the dispersion ranges from about 0.02 to 0.2, and more preferably from about 0.04 to 0.14.

The reference electrode used with the biosensor electrode during enzyme deposition is preferably AgCl/Ag. The potential applied across the electrodes during this process should be from about 1.1 to 1.4 volts versus the reference electrode. Such potential should be applied for a period of 40 to 80 minutes. The deposited enzyme on the electrode should have a thickness of from about 300 to 600 nm and more preferably from about 400 to 500 nm.

In the next step, a selected synthetic monomer is electropolymerized at the locale of the deposited enzyme so as to create a polymer layer which is intermingled with the enzyme. It is believed that the electropolymerization process causes the monomer to be oxidized at the surface of the electrode and encapsulates much of the enzyme. The thickness of the polymer layer formed is self-limiting, i.e., because the polymer is non-conducting, it cannot conduct electrons to become, in effect, an extension of the electrode. This means that the film will stop forming when communication with the electrode is interrupted.

The starting monomer for this step is selected with certain end properties in mind. Generally, the polymeric film should have a thickness and permeability consistent with the desired biosensor, but generally the polymeric layer should have a thickness of up to about 100 nm, and more preferably from about 10 to 100 nm. Second, the polymer film should have well-defined and reproducible permeability characteristics with optimal permeability for the enzyme substrate while excluding electroactive interferants such as ascorbate, urate and acetaminophen.

The single most preferred monomer for use in the electropolymerization step is phenol which should be present in an aqueous buffered phenol solution at pH 7. However, other candidate monomers include substituted and unsubstituted phenols. Preferred phenol monomers include 4-aminophenol, 1,4-dihydroxybenzene, 1,3-dihydroxybenzene, 1,2-dihydroxybenzene, 3-hydroxytyramine, 1,3,5-trihydroxybenzene, and 1,2,3-trihydroxybenzene.

In the electropolymerization procedure, the enzyme-deposited electrode is immersed in the monomer solution along with a reference electrode under an inert gas (e.g., argon) atmosphere. An appropriate potential is then applied to induce the electropolymerization reaction and create the desired polymer layer. In the next step of the preferred procedure, a silane film is applied over the polymer layer. This can be accomplished by dipping the electrode in a silane solution and applying a potential versus a reference electrode to enhance silane crosslinking. One suitable silane is (3-aminopropyl) trimethoxysilane, but other silanes such as 3-aminomethyl trimethoxysilane, 3-aminoethyl trimethoxysilane, 3-aminopropyl trimethoxysilane, 3-aminomethyl triethoxysilane, 3-aminoethyl triethoxysilane, and 3-aminopropyl triethoxysilane.

The next step in preparation of the sensor involves application of a polyurethane or other suitable coating over the silane film. This is done by dip-coating the electrodes with polyurethane solution in a suitable solvent and application of an appropriate potential versus the reference electrode. The final coating should have a thickness of from about 1 to 10 microns ($1–10\times10^{-4}$ cm).

Once the sensor outer coating is applied, the sensor is conditioned. In the sensor conditioning process, the completed sensor is first dried at 4° C. in a refrigerator for two or three days and is then transferred to a pH 7.4 phosphate buffered saline solution (0.05 M, containing 0.15 M NaCl). The buffer is changed every three days and the electrodes are conditioned continuously for two weeks with no potential applied to the electrodes. At the end of the two week period, the selectivity and sensitivity are measured and are hereafter referred to as the initial selectivity and initial sensitivity.

Sensors according to the invention should exhibit selectivity and sensitivity characteristics that are stable over a period of time. The selectivity characteristics of the polymer film should be stable for at least about 60 days, meaning that the selectivity should vary no more than ±10% relative to the initial selectivity over this time period. This feature of the polymer film is herein referred to as "selectivity stability." The polymer film should also serve to stabilize the sensor response over time thus leading to stable glucose response or sensitivity. The sensitivity of the complete sensor should not be lower than 90% of the initial sensitivity and should not drift more than 0.5% per day for at least about 60 days. This stability of the sensor sensitivity is herein referred to as "sensitivity stability."

Finally, the linearity of the resulting sensor should be greater than 92% for a glucose sensor, calculated as follows:

$$\% \text{ linearity} = \frac{\text{current response at 25 mM glucose/25 mM}}{\text{current response at 5 mM glucose/5 mM}} \times 100$$

BRIEF DESCRIPTION OF THE DRAWINGS

FIG. 10A is an AFM image of an enzyme membrane layer created by electrodeposition at 1.3 V vs. AgCl/Ag for 1 hour in a solution containing 10 mg/mL GOx, where the sample was scored with a razor blade to expose the electrode surface;

FIG. 10B is an AFM surface image similar to that of 10A except that the electrodeposition was carried out in the presence of 0.8 mM Triton X-100;

FIG. 10C is a thickness graph corresponding to FIG. 10A and illustrating the enzyme layer thickness of the sample;

FIG. 10D is a thickness profile graph corresponding to FIG. 10B and illustrating the enzyme layer thickness of the sample;

FIG. 11A is a hydrodynamic diameter spectrum (DLS) of a solution containing 10 mg/mL GOx in 50 mM phosphate buffer (pH=7);

FIG. 11B is a hydrodynamic diameter spectrum (DLS) of a solution containing 10 mg/mL GOx and 0.8 mM Triton X-100;

FIG. 11C is a hydrodynamic diameter spectrum (DLS) of a solution containing 0.8 mM Triton X-100 in 50 mM phosphate buffer (pH=7);

DETAILED DESCRIPTION OF THE PREFERRED EMBODIMENT

Figure 1:
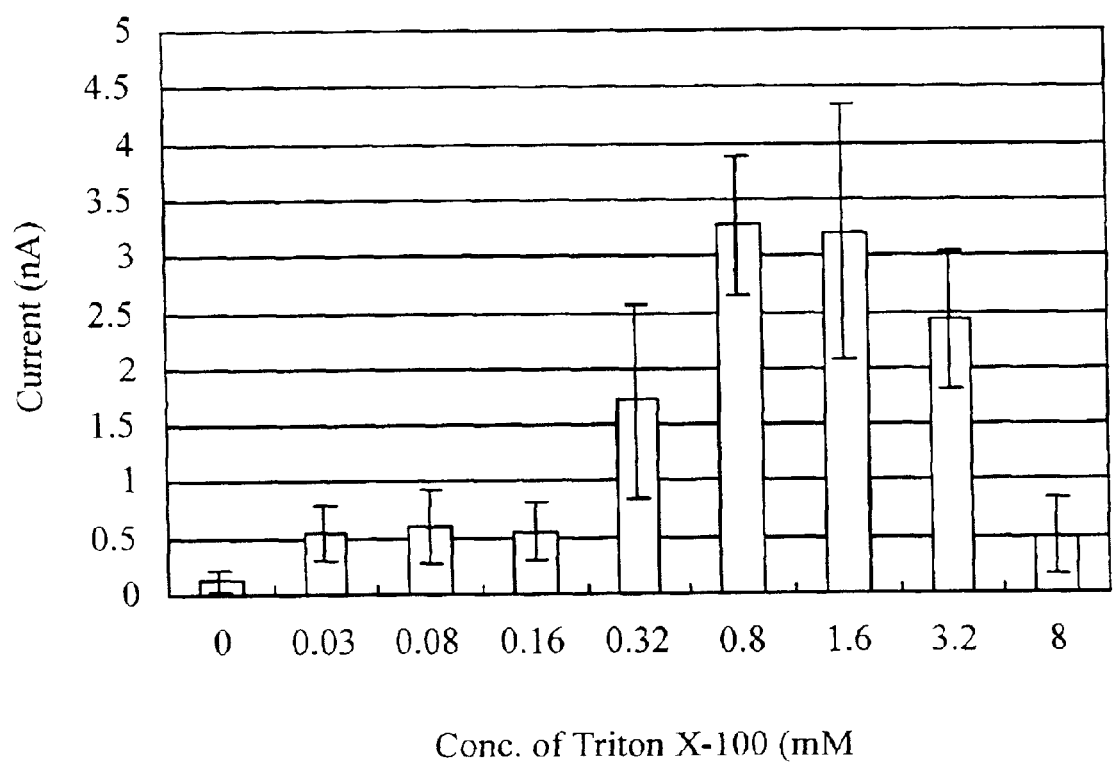
FIG. 1 is a bar graph illustrating the effect of Triton X-100 concentration on the electrodeposition of glucose oxidase as measured by the current response to 5 mM glucose (n=3), where the electrodeposition was performed at 1.3V vs. AgCl/Ag for 30 minutes in a solution containing 10 mg/mL GOx.

The following examples set forth methods for the deposition of glucose oxidase on a substrate, and for production of an implantable glucose sensor. It is to be understood, however, that these examples are provided by way of illustration and nothing therein should be taken as a limitation upon the overall scope of the invention.

EXAMPLE 1

In this example, preferred procedures for the electrodeposition of GOx onto Pt wire substrate are explained.

Materials

Glucose oxidase (GOx, EC 1.1.3.4, 277 U/mg) was purchased from Biozyme International (San Diego, Calif.). Triton X-100 was obtained from Sigma (St. Louis, Mo.). β-D(+) glucose, sodium hydrogen phosphate, and potassium dihydrogen phosphate were obtained from Fisher (Fair Lawn, N.J.). Deionized water used in these studies was prepared using a Barnsted Nanopure II system. All other chemicals used in this study were analytical grade.

Platinum disk microelectrodes were used to measure glucose response under a variety of deposition conditions. A Pt—Ir wire (90% Pt) obtained from Medwire (Mt. Vernon, N.Y.) was cut to 1 cm length, and washed with acetone under ultrasonication for 10 minutes. After connecting with a conducting Cu wire (4 cm) using silver epoxy (DOTITE, Type D-550, Fujikura Kasei Co., Ltd, Japan) the Pt—Ir wire was inserted into a glass capillary and sealed by heating. After sealing, the tip of the electrode was polished with sandpaper and with Al powder (1.0 and 0.3 micron, Micropolish®II, Buehler, Lake Bluff IL.) until all scratches on the electrode surface disappeared. The electrodes were cleaned by soaking in 1M HCl—$HNO_3$ (1:1) for twenty minutes and then rinsed with a large amount of deionized water. The diameter of the disk electrode was 170 $\mu$m. The uniformity of each electrode was checked by measuring the peak current corresponding to the cyclic voltammetric oxidation of 1 mM $Fe(CN)_6^{4-}$. The current variation for the electrodes using this approach was less than 5%.

Apparatus

All electrochemical measurements were made with a CH Instruments (Austin, Tex.) Model CHI422 Electrochemical Analyzer connected to a Dell Dimension XPS B800r computer. This instrument was also interfaced to an Electrochemical Quartz Crystal Microbalance (EQCM) provided by CH Instruments.

The EQCM consisted of a Teflon cell 37 mm high and 35 mm in diameter with a total volume of 4 mL. Pt coated AT-cut crystals (crystal diameter, 14 mm; oscillation frequency, 7.995 MHz; obtained from International Crystal Manufacturing, Oklahoma City, Okla.) were employed in this study except as noted. Each crystal had an etched (3–5 $\mu$m roughness) surface and Pt was directly deposited on it (thickness, 100 nm; electrode area, 0.196 $cm^2$). A AgCl/Ag reference and a gold counter electrode (50 $mm^2$) were employed. The system was allowed to equilibrate for about one hour while the crystal frequency became stable. The system was calibrated by deposition of Ag. To avoid silver chloride precipitation, a silver wire (diameter, 0.5 mm; length, 10 cm) was used as the reference instead of AgCl/Ag. The electrodeposition was performed by applying 0.0 V vs. Ag in 1.0 mM $AgNO_3$ (with 0.1 M $KClO_4$) under Ar atmosphere for 30 sec. From the relationship between frequency change and total charge from a cathode deposition of Ag, a sensitivity of 1.4 ng/Hz was obtained. The maximum mass change measurable is about 1500 ng. For the AFM studies of film thickness, Pt-quartz crystals (100 mm Pt film deposited on AT-cut polished quartz (Freq: 9.995 MHz)) were employed. The sensitivity was 0.9 ng/Hz.

Atomic force microscopy was carried out using a Nanoscope® E (Digital Instruments, Santa Barbara, Calif.). A silicon nitride tip was used as a detection probe (NANOPROBE™ SPM Tips, Type DNP-20, spring constant, 0.06 N/m; cantilever length, 100 $\mu$m; Cantilever configuration, V-shaped; Tip radius of curvature, 20–60 nm; Sidewall angles, 35° on all 4 sides). Each image was processed and analyzed through built-in software (NanoScope V.4.1). Dynamic light scattering was conducted using a Brookhaven Instruments Model BTC9865 (Holtsville, N.Y.) system. The system components include a Model BI-200SM goniometer, 532 nm diode laser, and a thermostated cell holder. The scattering angle was set at 90°. Post-acquisition data evaluation was carried out using a BI9000AT digital autocorrelator. The system was calibrated using a polystyrene nanosphere standard (96±3.1 nm) (Duke Scientific, Palo Alto, Calif.). Zeta potential and mobility analysis for enzyme in buffer solution were carried out using a Zeta Potential Analyzer (BIC Zeta PALS, Brookhaven Instruments Co., Holtsville, N.Y.). Data were calculated with software provided by the manufacturer.

Methodology

Enzyme electrodeposition was carried out by potential step chronoamperometry (I-t curve mode), using an 10 mg/ml solution of enzyme with an enzyme concentration of $6\times10^{-5}$ M. In each trial, the initial potential was set at 0.3 V vs. AgCl/Ag. After 10 sec of initial holding, the potential was stepped to the defined value. Current data were taken every 0.2 sec. The Pt—Ir disk electrode was placed in a 50 mM phosphate buffer saline solution, pH 7.0, containing variable amounts of GOx and Triton X-100. The volume of each solution was 0.5 mL and a AgCl/Ag electrode was used as a reference and a Pt—Ir wire used as the counter electrode. After the electrodeposition was carried out, the electrode was removed from solution and dried in air for 10 minutes. The electrode was then immersed in deionized water and washed by agitation.

The response of sensors to glucose was established by immersing each sensor in 10 mL of phosphate buffered saline (PBS, 0.1 M, pH 7.4). A potential of 0.65 V vs. AgCl/Ag electrode was then applied to the sensor. After the background current became stable (at least 10 min), glucose was added to produce sequential 5 mM increases in concentration.

For atomic force microscopy measurements, the x, y and z-axis were calibrated using a calibration standard of inverted pyramids (5 $\mu$m length, 200 nm depth, Digital Instruments, Santa Barbara, Calif.). The enzyme was deposited on platinum quartz crystals (AT-cut polished quartz, total diameter—14 mm, electrode area—0.196 $cm^2$, electrode thickness—100 nm using the same cell as for the EQCM measurements. Crystals were rinsed with acetone before electrodeposition, which was carried out at 1.3V vs. AgCl/Ag for one hour in 50 mM phosphate buffer (pH 7.0) containing 10 mg/mL GOx with and without 0.8 mM Triton X-100. After electrodeposition, each electrode was carefully washed with deionized water and stored under dry conditions in the refrigerator. AFM measurements were made on the dry film 24 hours later.

Effect of Triton X-100 on Electrodeposition

Figure 2:
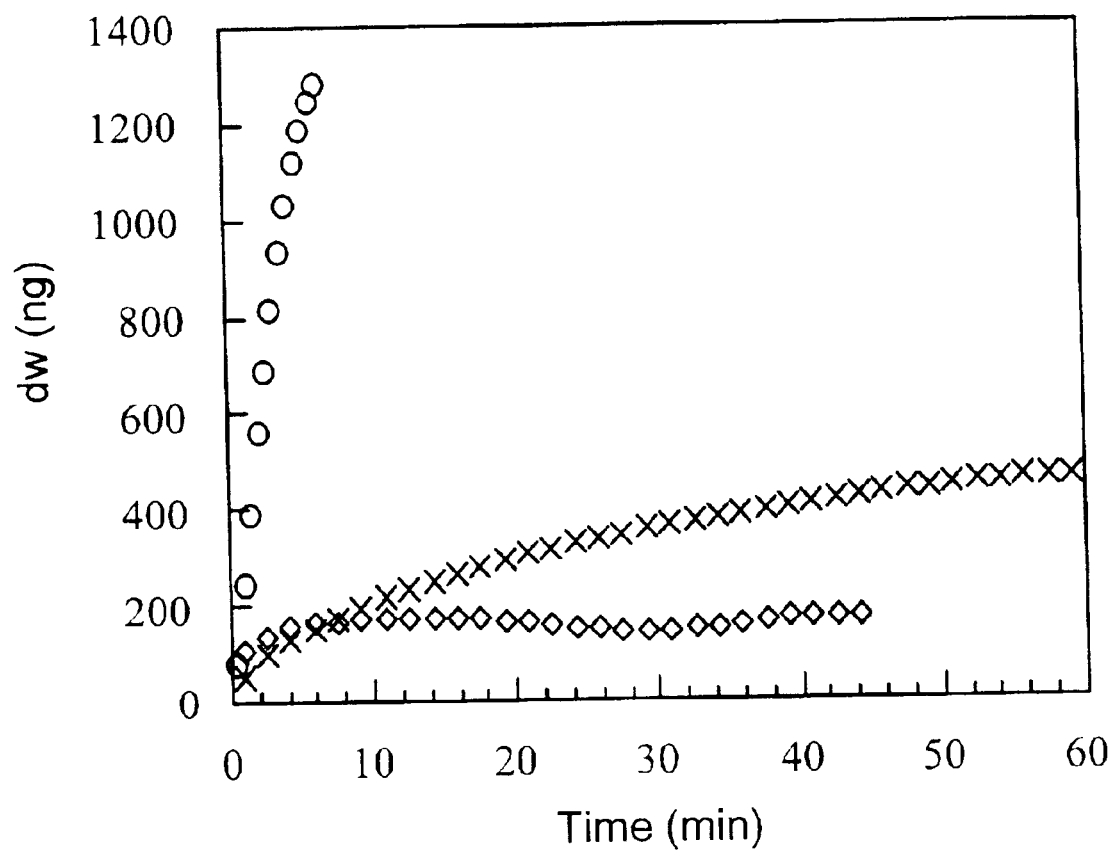
FIG. 2 is a graph illustrating EQCM mass changes during electrodeposition of GOx at different Triton X-100 concentrations, where the concentration was 0 mM (x), 0.8 mM (○) and 8 mM (◇)

FIG. 1 illustrates the dependence of current response to 5 mM glucose at a Pt—Ir electrode on which GOx has been deposited in the presence of variable concentrations of Triton X-100. In the absence of the non-ionic detergent the response is extremely low and the optimal response occurs between about 0.32 and 3.2 mM detergent. No enhancement of deposition is observed if certain types of cationic (cetyltrimethylammonium chloride) or anionic detergents (sodium dodecylsulfate) are employed. FIG. 2, obtained from EQCM measurements, confirms that the deposition of enzyme is strongly influenced by the presence of a compatible detergent. Some deposition can occur in the absence of detergent so that after 60 minutes about 450 ng is deposited. If the detergent concentration is too high, the amount of electrodeposited enzyme is significantly reduced. The critical micelle concentration of Triton X-100 is 0.2 mM, and most efficient enzyme deposition occurs above that value.

Effect of Potential on Sensor Response

Figure 3:
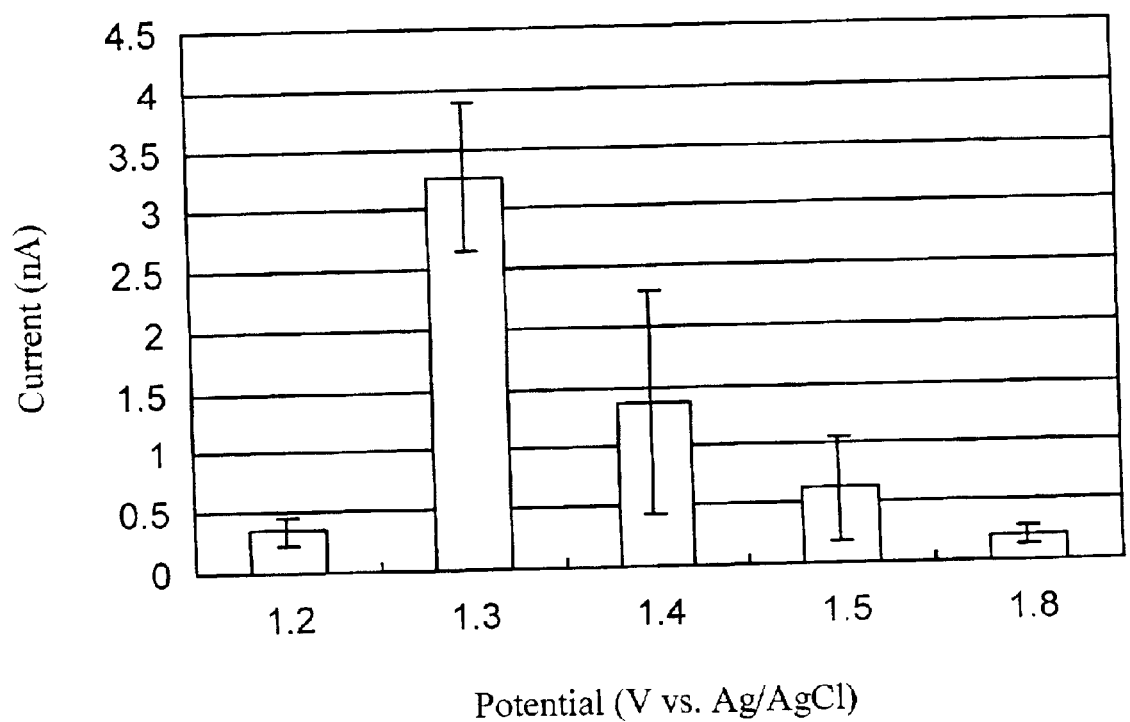
FIG. 3 is a graph illustrating the effect of applied electrodeposition potential on current response to 5 mM glucose (n=3), where the electrodeposition was performed for 30 minutes in a solution containing 10 mg/mL GOx and 0.8 mM Triton X-100.
Figure 4:
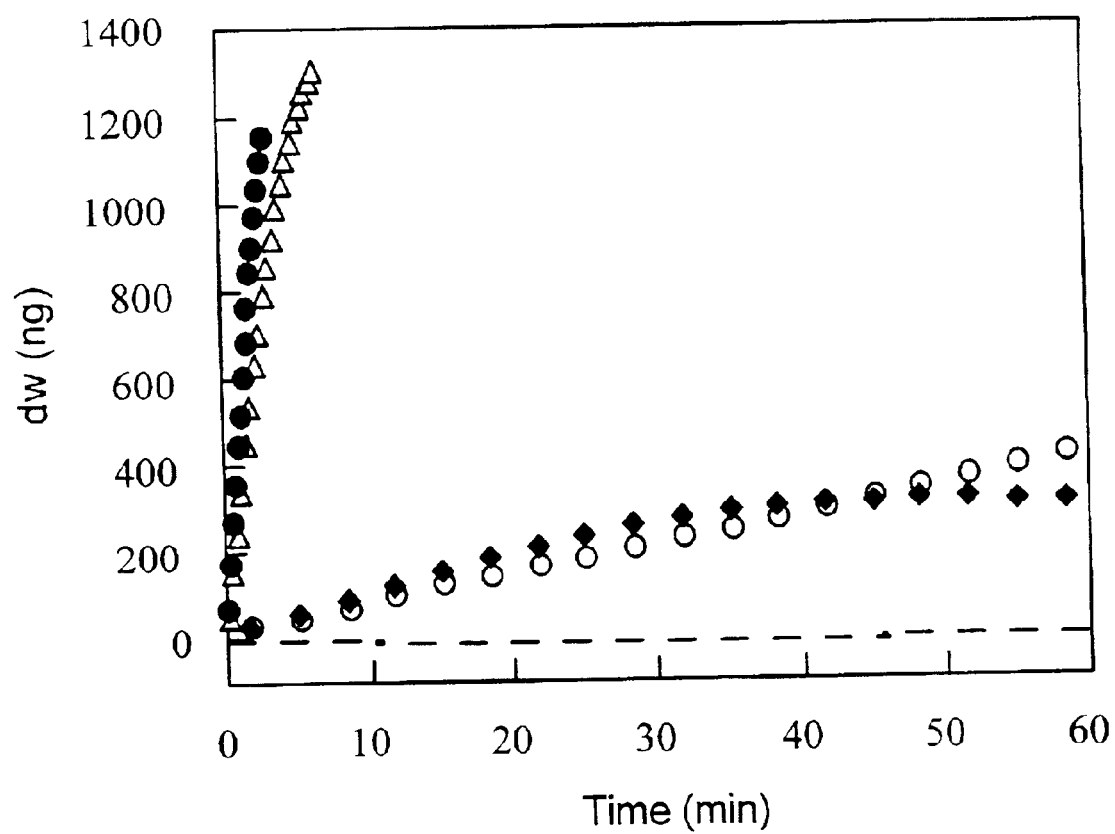
FIG. 4 is a graph illustrating EQCM mass changes during electrodeposition of GOx at different potentials, using the conditions specified in the FIG. 3 description, where applied potentials were 1.0 V (○), 1.2 V (♦), 1.3 V (△) and 1.4 V (●) vs. AgCl/Ag, and where the broken line corresponds to the response at the rest potential.
Figure 5:
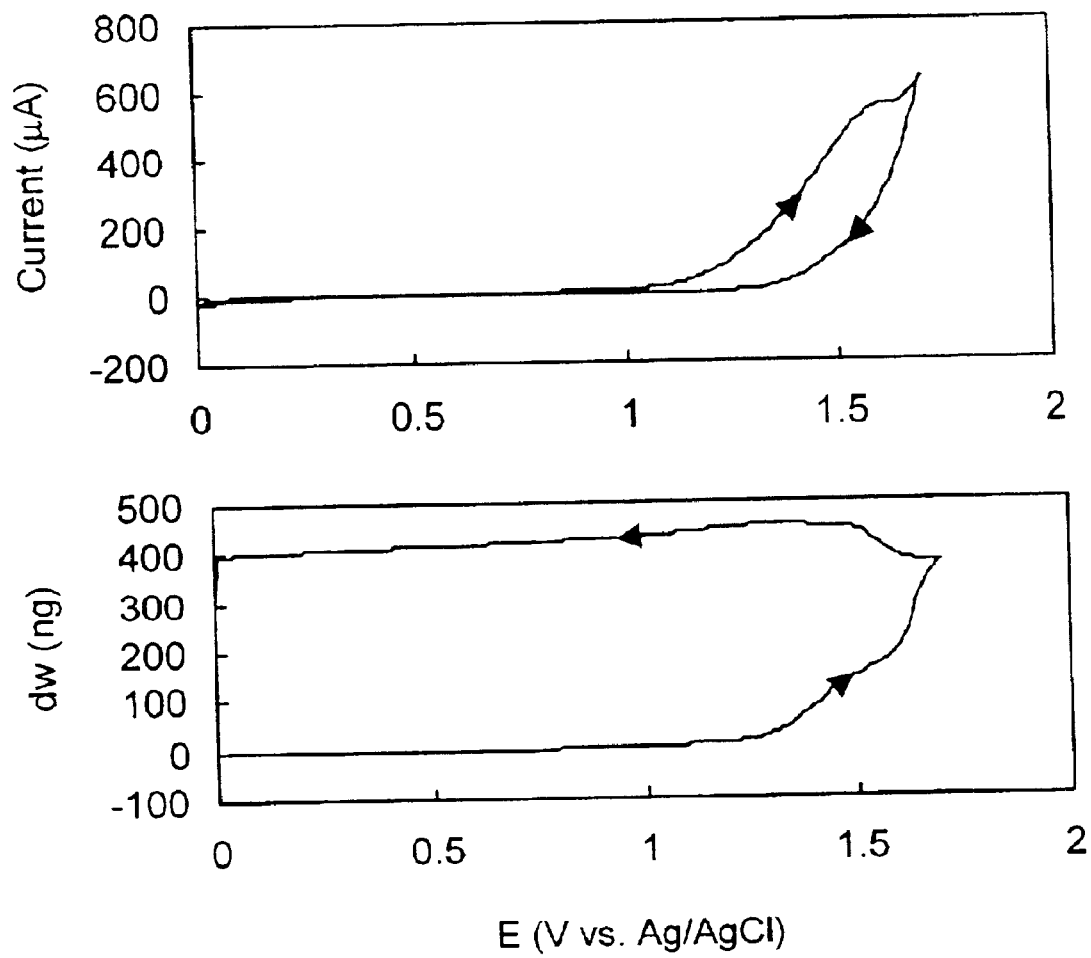
FIG. 5 is a pair of corresponding graphs showing current (top graph) and mass change profiles (bottom graph) obtained from cyclic voltammetry using the EQCM system, the conditions specified in the description of FIG. 3, and a scan rate of 10 mV/sec.

FIG. 3 shows the effect of the applied electrodeposition potential on the apparent activity of the immobilized enzyme. As indicated, the maximum current is obtained at 1.3 V vs. AgCl/Ag reference, suggesting that this is the potential at which the maximum amount of enzyme is deposited. The FIG. 4 graph demonstrates that above an applied potential of 1.2 V, the rate of deposition of enzyme increases rapidly. FIG. 5 is a voltammogram in which the potential dependence of enzyme deposition is further illustrated. It may be that some of the enzyme deposited at higher potentials is not active, or the response as measured from the evolving hydrogen peroxide is not correct; it is believed the latter to be the case. Hall, et al.; *Electrochim. Acta* 1997, 43, 579–588 demonstrated that the oxidation of hydrogen peroxide is electrocatalytic and depends on an electrode surface with $Pt(OH)_2$ functionalities. The applied potential region for enzyme deposition corresponds to the region of water oxidation. It is a region in which platinum oxide is formed which is not beneficial to peroxide oxidation. This is illustrated by the results shown in Table 1. The control sample corresponds to the current obtained at a Pt—Ir electrode for a 50 μM peroxide solution at an applied potential of 0.65 V. This is the effective concentration that would be measured if peroxide were generated from the enzyme-catalyzed reaction. If, however, a potential of greater than 1.0 V is applied to the electrode as required for enzyme electrodeposition, and then returned to 0.65 V, the response to peroxide is much lower. Pt oxides deposited on Pt electrodes tend to be stabilized by the presence of adsorbed films. Zhang, Y., et al., J. Electroanal. Chem. 1993, 345, 253–271.

TABLE 1

Effect of potential application in a 50 mM phosphate buffer for 30 min. on current response to $H_2O_2$ at Pt—Ir electrode (n = 3)

| applied potential (V vs AgCl/Ag) | response to 50 μM $H_2O_2$ (nA)* | Std. Dev. | % ratio against control |
|---|---|---|---|
| control | 10.22 | 1.89 | 100 |
| 1.2 | 2.37 | 0.56 | 23.1 |
| 1.3 | 1.30 | 0.08 | 23.1 |
| 1.4 | 0.66 | 0.13 | 6.5 |
| 1.5 | 0.54 | 0.05 | 5.3 |
| 1.8 | 0.09 | 0.02 | 0.9 |

*Applied potential, 0.65 V vs. AgCl/Ag

Effect of Enzyme Concentration on Electrodeposition

Figure 6:
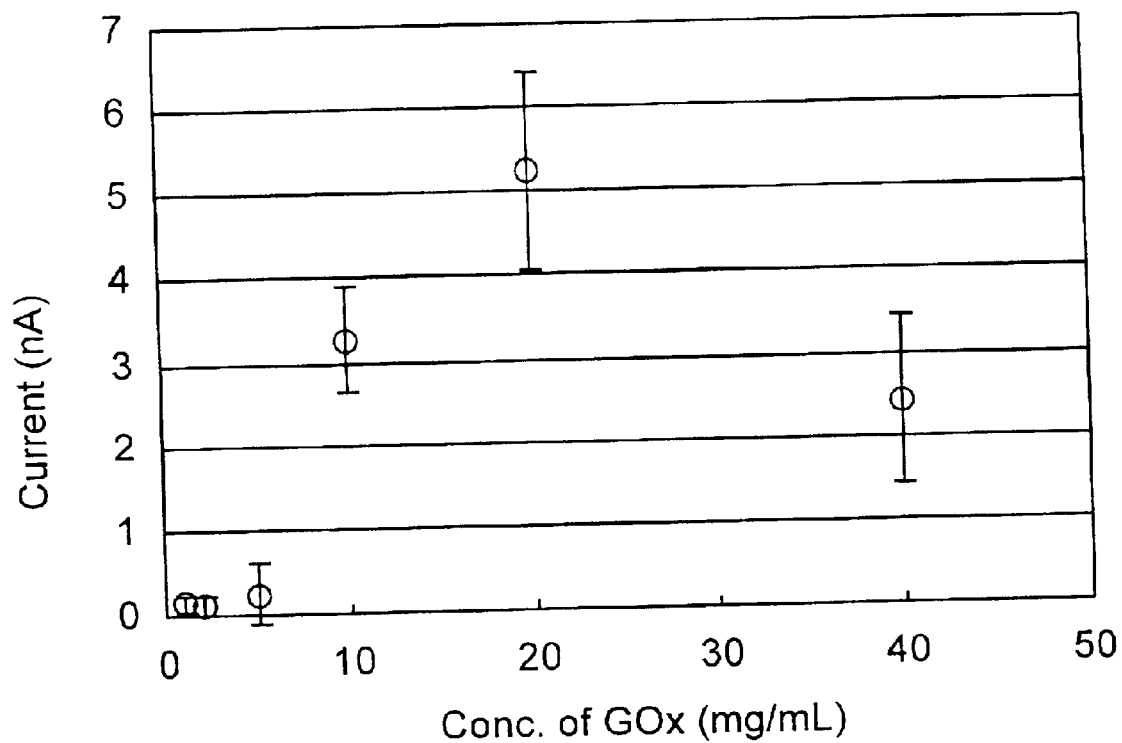
FIG. 6 is a graph depicting the effect of GOx concentration on electrodeposition as reflected in the current response to 5 mM glucose (n=3), where the Triton X-100 concentration in the solution was 0.8 mM.
Figure 7:
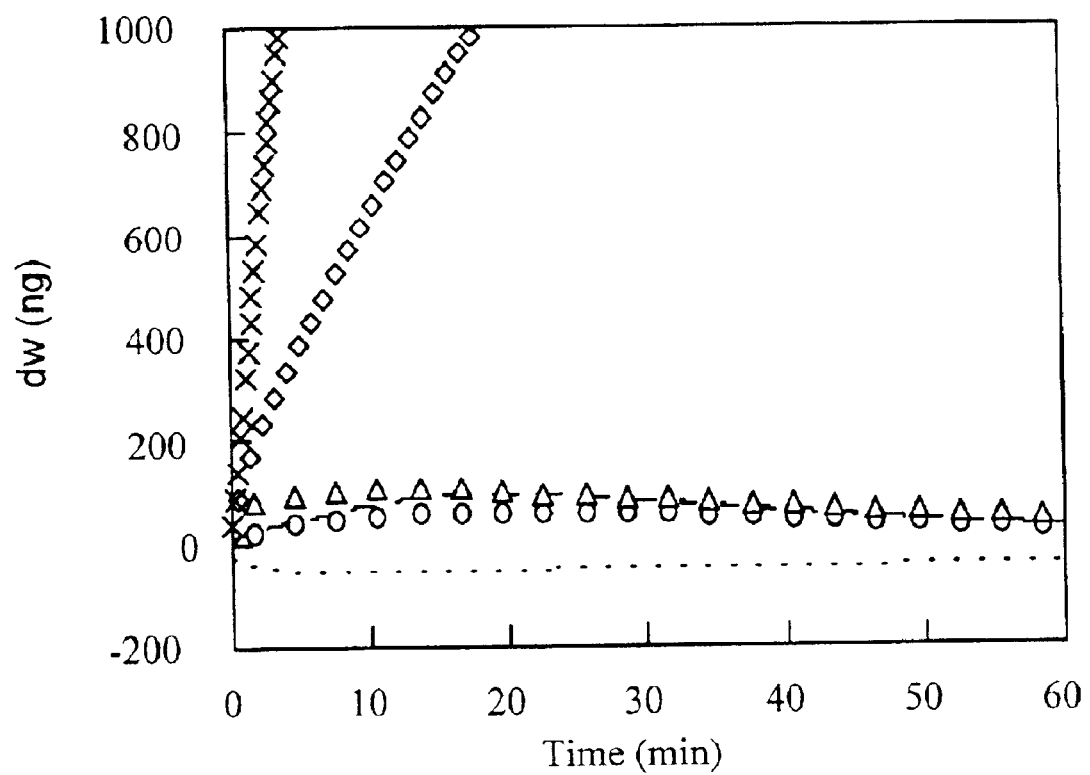
FIG. 7 is a graph illustrating EQCM mass changes during electrodeposition at varied GOx concentrations, where the electrodeposition was performed at 1.3 V vs. AgCl/Ag in a solution containing 0.8 mM of Triton X-100, with a GOx concentration of 0 mg/mL (broken line), 2 mg/mL (○), 5 mg/mL (△), 7 mg/mL (◇) and 10 mg/mL (x), with the dashed line being GOx without Triton X-100.

As shown in FIG. 6, the current due to the immobilized enzyme increases rapidly with increasing GOx concentration. At very high enzyme concentrations the amount of immobilized enzyme actually decreases. A possible reason for the decrease in amperometric signal for GOx concentrations higher than 20 mg/mL may be related to the stoichiometry of GOx and Triton X-100. In FIG. 6 the mean current for 40 mg/mL GOx is 2.5 nA for a detergent concentration of 0.8 mM. If this concentration is increased to 1.6 mM, the mean current doubles to 5.0 nA. The uptake of enzyme onto the electrode is similarly reflected in the EQCM results shown in FIG. 7.

Effect of Electrodeposition Time on Sensor Response

Figure 8:
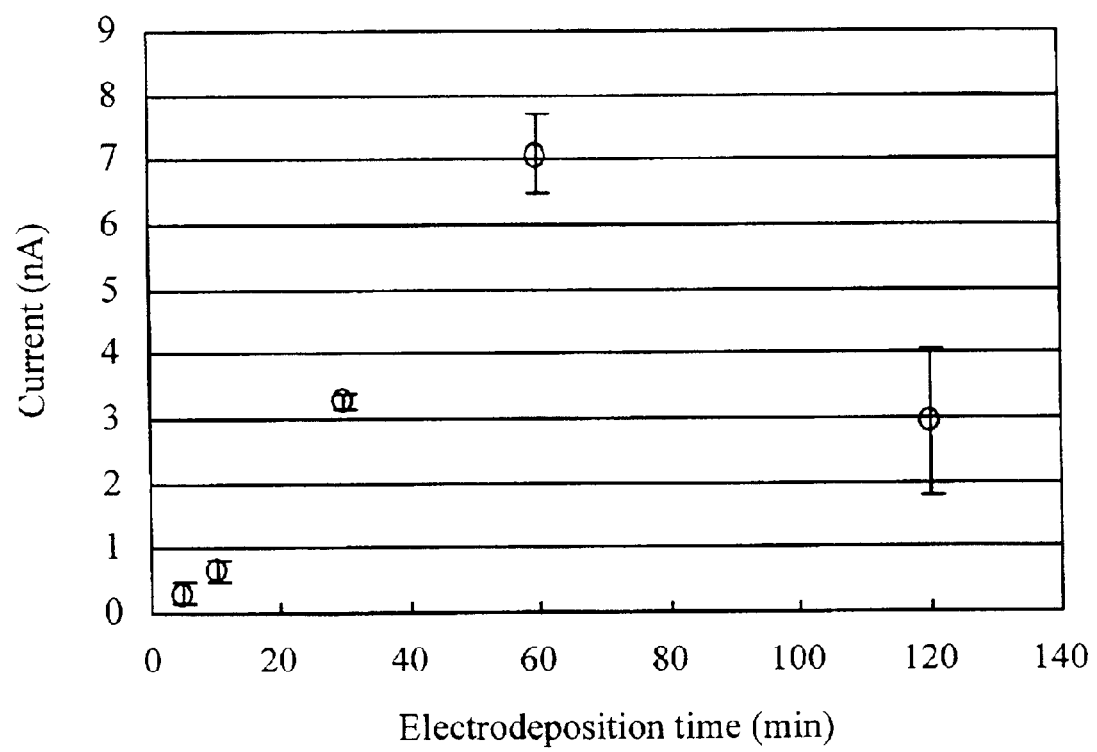
FIG. 8 is a graph of electrodeposition time versus current in response to 5 mM glucose (n=3), where each electrodeposition was performed at 1.3 V vs. AgCl/Ag in a solution containing 10 mg/mL GOx and 0.8 mM of Triton X-100.

FIG. 8 shows the relationship between the sensor response current as a function of deposition time under otherwise optimized conditions. The current increases linearly with deposition time up to one hour. However no further current increase was observed beyond this point. The current response to 50 μM $H_2O_2$ on a bare Pt—Ir disk electrode after 2 hour polarization at 1.3 V vs. AgCl/Ag, was 1.13 nA, almost the same as that for 30 min polarization under the same conditions (Table 1). The current decrease observed at 2 hours of electrodeposition in FIG. 8 probably resulted from the loss of enzyme activity suffered from exposure to low local pH conditions for an extended time.

Morphology of the Enzyme Layer

Figure 9A:
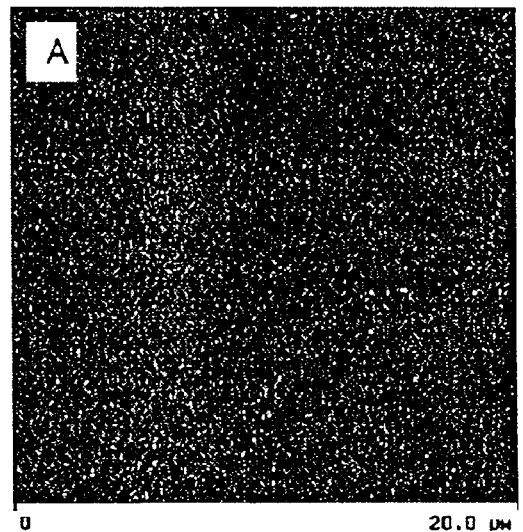
FIG. 9A is an AFM electrode surface image of a bare gold electrode.
Figure 9B:
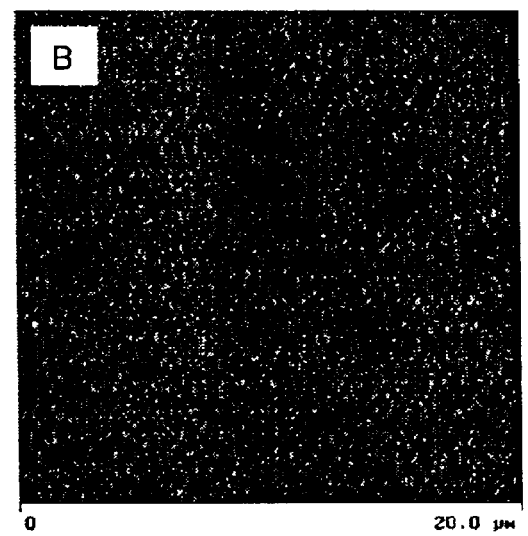
FIG. 9B is an AFM electrode surface image of GOx electrodeposition without Triton X-100.
Figure 9C:
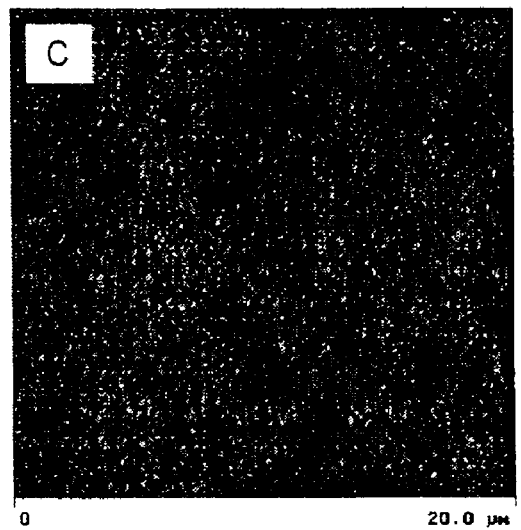
FIG. 9C is an AFM electrode surface image of GOx electrodeposition with 0.8 mM Triton X-100.

The thickness and roughness of the enzyme layer created by electrodeposition on a gold electrode was estimated using AFM. FIGS. 9A through 9C show AFM images for the enzyme layer after one hour of electrodeposition in GOx solution with and without 0.8 mM Triton X-100. FIG. 9A shows the polycrystalline platinum surface without enzyme present. When electrodeposition is carried out in the absence of detergent (FIG. 9B), the AFM of the dry film reflects the features of the underlying substrate, with a correspondingly smooth film. By contrast, the layer in FIG. 9C appears rougher. FIGS. 10A–10D show the results of depth profiling of the electrodeposited films. FIG. 10C indicates a thickness of the enzyme layer of about 25 nm, corresponding to deposition of the film in the absence of detergent. By contrast, the thickness of the enzyme layer where detergent is used (FIG. 10D) is about 480 nm. The dimensions of glucose oxidase, taken from the x-ray structure, are reported as 60 Å×52 Å×77 Å (Hecht, H. J. et al.; *J Mol Biol* 1993, 229, 153–172). The thickness of a GOx monolayer thus would be about 10 nm. In the absence of detergent, about 2 equivalent monolayers are formed. If the area occupied by a single GOx molecule is assumed to be $8 \times 10^{-13}$ cm$^2$, the total weight of a monolayer on the electrode should be about 66 ng. However, from FIG. 2 the total mass change is about 450 ng. Some of the mass gain is due to uptake of water and counterions. The total mass gain in the presence of detergent could not be measured because it exceeded the capacity of the EQCM (the mass change should be at least 3168 ng (66×48). The estimated film thickness for dry films will swell significantly on hydration so that the operating thickness of the GOx could increase by as much as 100–200%.

Solution Properties of GOx and Triton X-100 Micelles in Solution

In order to investigate the interactions between GOx and Triton X-100 in solution, dynamic light scattering experiments (DLS) were carried out. Prior to measurements, the 50 mM phosphate buffer solution was filtered through a 0.22-micron filter to remove dust particles. As shown in FIG. 11, the hydrodynamic diameter of GOx is about 10 nm, consistent with the X-ray results. Triton X-100 is observed to have a similar diameter at concentrations above its CMC (FIG. 11b), nearly equal to the reported value of 8–9 nm at 25° C. When the GOx and detergent are mixed together a somewhat broader distribution is observed but with approximately the same peak maximum. (FIG. 11c) There is also a peak at about 5 nm, and since it does not appear in the spectrum of either the enzyme or detergent alone, it is believed to result from the interaction of GOx and the detergent.

The Mechanism of Electrodeposition and the Role of the Detergent

Figure 12A:
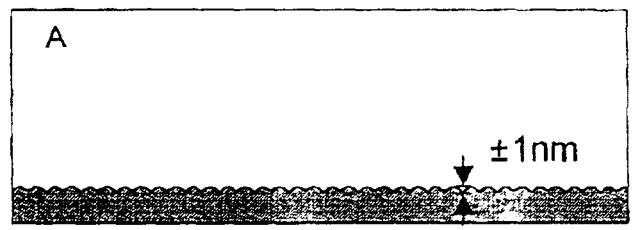
FIG. 12A is a schematic representation of the bare electrode profile measured by AFM.
Figure 12B:
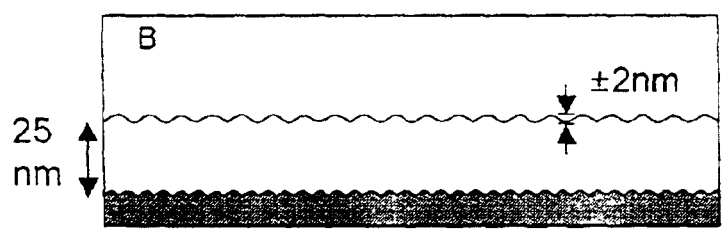
FIG. 12B is a schematic representation of the GOx enzyme layer profile measured by AFM for electrodeposited GOx without Triton X-100.
Figure 12C:
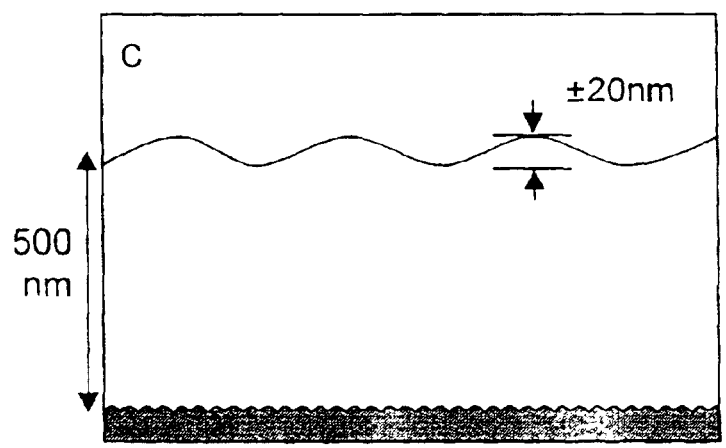
FIG. 12C is a schematic representation of the GOx enzyme layer profile measured by AFM for electrodeposited GOx with Triton X-100.

Although enzyme can chemisorb on the electrode surface, the dramatic influence of applied potential is quite evident as it produces a much more extensive and compact enzyme deposit. Notwithstanding the fact that the enzyme is negatively charged at pH 7, and the electrode positively charged, it is believed that electrophoretic (migration) effects in 50 mM phosphate buffer are rather unimportant. The zeta potential of GOx in this medium was measured as −0.4 mV, and this corresponds to an enzyme mobility of $3.5 \times 10^{-2}$ (μm/sec)/(V/cm). This mobility was much smaller than that for $HPO_4^{2-}$ or $H_2PO_4^-$ (3.4 (μm/sec)/(V/cm)), which were dominant anion species in the solution. The ion mobility of the enzyme is two orders of magnitude lower than the supporting electrolyte. When the relative concentrations are taken into account, it can be seen that the electrophoretic migration of the enzyme is negligible. The driving force for immobilization is the precipitation of enzyme on the electrode surface as a consequence of a local pH decrease created by the evolution of oxygen (oxidation of water) (Im, D. M., et al.; *Sens. Actuators*, B 1995, B24, 149–155). The linear increase in mass of deposited enzyme is further consistent with evolution of protons. The Triton X-100 micelles are the same size as the GOx molecules and therefore can suppress aggregation of enzyme and may easily substitute in a pseudolattice formed as the enzyme is deposited. It is possible that enzyme molecules eventually replace many of the detergent micelles in the deposited structure. There is a clear contrast between deposition of enzyme in the presence and absence of detergent. In the latter case about two monolayers of protein are formed as depicted in FIG. 12(a). The surface features of the substrate are preserved. The deposition process thus appears to be self-limiting. If too much detergent is added then the deposition process is inhibited. The detergent micelles, helpful for promotion of deposition, minimize aggregation of enzyme, and probably initially shield it from the very high electric field gradient at the electrode/solution interface. The detergent may also serve to slow down the deposition and make it more uniform, performing the analogous function of surfactants in electroplating. It is also possible that the micelles once deposited are in an environment below the CMC in which case each micelle should break up into over 100 individual detergent molecules (Brown, W., ed., *Light Scattering: Principles and Development*, Oxford University Press, New York, 1996; Rharbi, Y.; Li, M.; Winnik, M. A.; Hahn, K. G. *J. Am. Chem. Soc.* 2000, 122, 6242–6251). The enzyme layer deposited in the presence of the detergent is almost 25 times thicker (FIG. 12) and shows surface irregularities equivalent to almost 2 enzyme molecules. The presence of detergent on the electrode surface does not interfere either with the oxidation of water or the oxidation of hydrogen peroxide. In each case a small molecule must diffuse through the deposited enzyme layer.

This example demonstrates the electrochemically-mediated deposition of enzyme on an electrode promoted by the presence of a non-ionic detergent. Under these conditions a uniform and biologically active film is formed. It is then possible, using electropolymerization of small organic molecules through the already deposited enzyme layer, to generate a stable permselective film, as described in Example 2.

EXAMPLE 2

In this example an implantable glucose sensor in accordance with the invention was constructed and tested.

Reagents

Glucose oxidase (GOx, E.C. 1.1.3.4.) was obtained from Biozyme Laboratories International Ltd, CA. Phenol and (3-aminopropyl)trimethoxysilane (3-ATS) were purchased from Fluka (N.Y.). N-propyl trimethoxysilane was obtained from United Chemical Technologies (Bristol, Pa.). D-glucose (Glu) (from Sigma) solutions were allowed to mutarotate for 24 h before use. Acetaminophen (AP), L-ascorbic acid (AA) and uric acid (UA) were obtained from Aldrich and prepared immediately before testing, as they are subject to oxidative decomposition in solution. Teflon-coated platinum (Pt) (Pt(90%/Ir(10%)) wire (0.17 mm diameter) was purchased from Medwire Corp. (Mount Vernon, N.Y.). Polyurethane was obtained from Thermedics Inc. (MA) 0.05 M phosphate buffer was prepared from the corresponding phosphate salts. Phosphate-buffered saline (PBS) pH 7.4 was prepared from phosphate salts (0.1 M) and sodium chloride (0.15 M).

Apparatus

Amperometry was performed using a Model 814 Electrochemical Detector (CH Instruments, Texas) connected to a Dell (L500r) computer. Electrochemical quartz crystal microbalance (EQCM) measurements were made on a Model 422 Electrochemical Analyzer (CH Instruments, Texas) as described in Example 1. Pt wire and AgCl/Ag were used as counter and reference electrodes, respectively.

Sensor Preparation

One end of a 5 cm long Teflon-coated Pt wire (0.17 mm diameter) 10 (see FIG. 13) was stripped over a 1 mm length to expose the metal surface 12 as a sensing cavity 14. This was achieved by first scribing a circular cut in the Teflon coating (35-μm thick) 5 mm from the tip and then sliding the Teflon out to create a cavity of 1-mm length. The excess Teflon at the tip was trimmed off and the tip was sealed off with epoxy glue (Super Glue Corp., CA). The area of the exposed Pt wire within cavity 14 was 0.534 mm$^2$. The other end of the wire 10 was stripped by 1 cm to provide a connection to the potentiostat. The sensing cavity 12 of the Pt—Ir wire was cleaned by dipping into 1 M HNO$_3$/1 M HCl and 1 M NaOH solution for 20 min, respectively. Copious rinsing with deionized water followed. A three-electrode system was employed with the Pt wire working electrode, AgCl/Ag (3 M NaCl) reference electrode and a large Pt wire as counter electrode.

Figure 13:
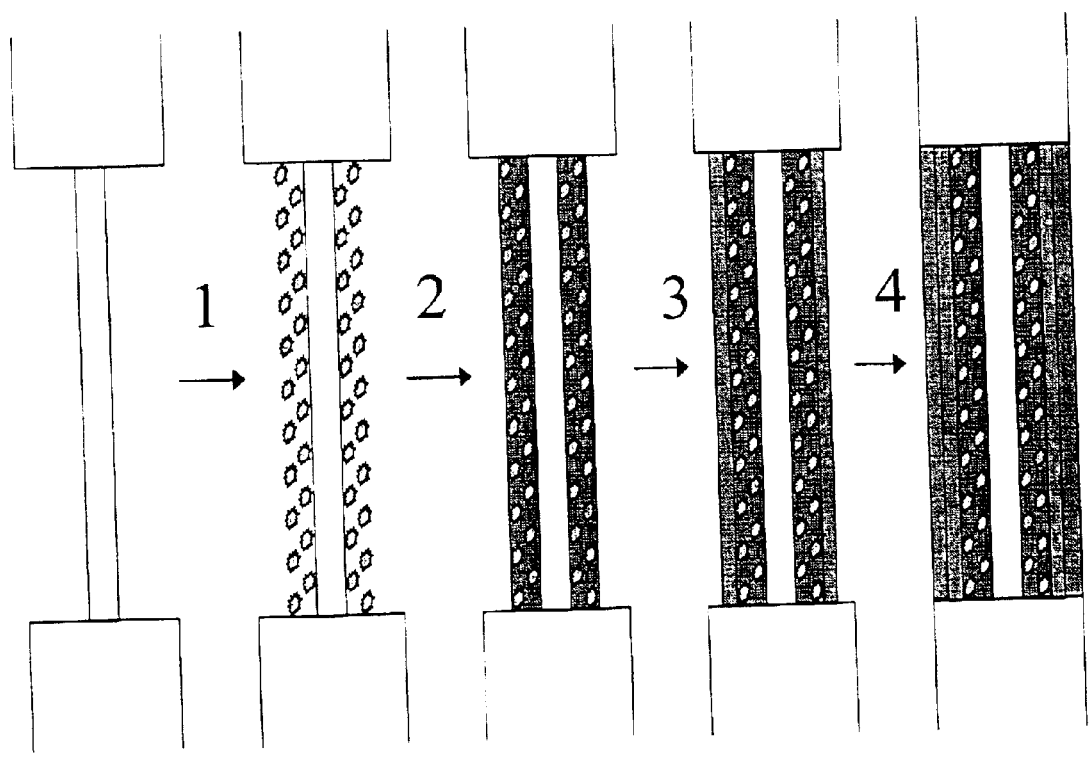
FIG. 13 is a schematic diagram illustrating the steps involved in the preferred process for the preparation of an oxidase enzyme biosensor.

The procedures for preparing a GOx electrode are shown in FIG. 13. Step 1—10 mg/mL GOx solution in pH 7.0 phosphate buffer (0.05 M, containing 0.02% (v/v) Triton X-100) was used for the electrodeposition of a layer of GOx on the Pt—Ir electrode. A potential of 1.3 V (vs. AgCl/Ag) was applied to the Pt electrode for 1 h. This step is more fully explained in Example 1. Step 2—The Pt electrode with the GOx layer 16 was put into 40 mM phenol solution in pH 7.0 buffer (previously degassed with argon for at least 20 min) and an argon atmosphere was maintained during this step. A 0.9 V (vs. AgCl/Ag reference) was applied to the electrode for 15 min to induce the electropolymerization reaction and creation of a polyphenol layer 18 intermingled with the GOx layer 16. Step 3—The Pt electrode was dipped into 10 mM 3-ATS solution and 0.6 V (vs. AgCl/Ag reference) was applied for 15 min to enhance the cross-linking of ATS and creation of an ATS layer 20 onto the polyphenol layer 18. By adjusting the variables involved in the preparation of the enzyme electrodes, the analytical performance thereof with regard to both glucose measurement and interference removal can be controlled. Step 4—Finally, polyurethane film was loaded onto the electrode by dip-coating the electrodes with 3% (w/w) polyurethane (PU) solution in 98% tetrahydrofuran (THF)-2% dimethylformamide (DMF) (w/w) to create the outer layer 22. Most of the organic solvent was allowed to evaporate on the loop before the film was coated onto the electrodes. For the electrochemical measurements, the sensor was dipped into a cell consisting of 5 mL of pH 7.4 PBS buffer at room temperature and a potential of 0.65 V (vs. AgCl/Ag) was applied for the amperometric glucose detection with stirring. The background current was allowed to stabilize before measurement.

Electrodeposition of GOx on the Pt Electrode

The electrodeposition of enzyme facilitates control of sensor sensitivity and can be carried out under mild conditions, making this procedure very suitable for a range of biomolecules. Electrodeposition of GOx (together with BSA) on electrodes has been accomplished by constant current (Strike, et al., *Sensors & Actuators*, 1993, B 13, 61–64) or fixed potential (Im, D. M., et al.; *Electrochim.*

Acta 1996, 41, 2433–2439). The latter approach was found more effective. Variation of the applied potential has been shown to influence the characteristics of enzyme electrodes. It has been reported that a large amount of GOx could be electrodeposited in the oxygen-evolution region (above 1.0 V) (vs. AgCl/Ag)) [23b]. It was found that a potential of 1.3 V to be optimal for the electrodeposition.

Acetaminophen is often used as a performance standard because it is a difficult electrochemical interference to eliminate. It is therefore chosen as a primary test of electrochemical specificity. The choice of 1.3V for the electrodeposition potential proved to give the highest ratio of enzyme activity (measured by the current due to peroxide oxidation) and also high selectivity against acetaminophen (Glu/AP) as shown in FIG. 2. EQCM experiments showed that the extrapolated mass increase on the Pt-coated quartz was 280.36 ng/mm$^2$. Considering the electrode area of 0.534 mm$^2$ and a GOx molecular diameter of 8~9 nm (Wilson, R.; et al., *Biosens. Bioelectron.* 1992, 7, 165–185), the thickness of the GOx layer was about 0.5 μm under the electrodeposition conditions of this example (1.3 V for 1 h). It was found that a biosensor prepared by GOx adsorption only showed very small response to glucose (FIG. 2), which meant the physisorption of GOx on the electrode could be neglected compared with electrodeposition at 1.3 V.

Selectivity of Pt Electrodes Modified with Polyphenol and 3-ATS Films

Figure 14:
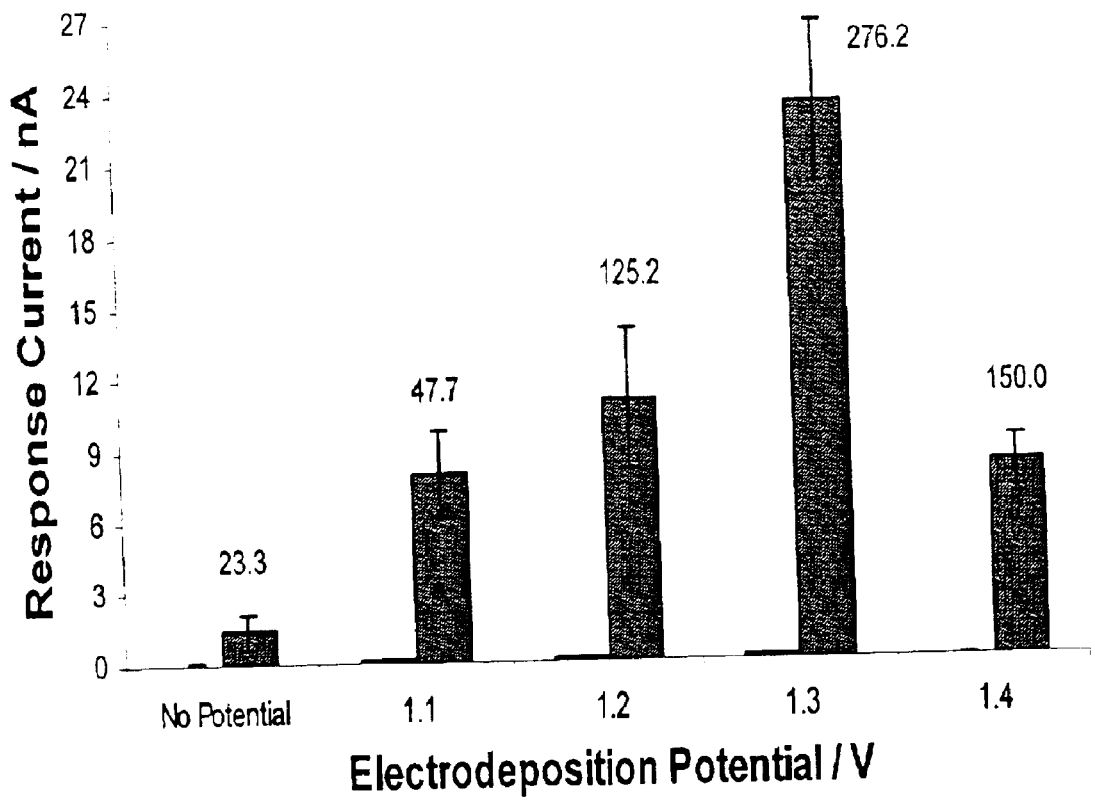
FIG. 14 is a graph illustrating the effect of electrodeposition potential for GOx on peroxide response of the electrode (n=3) where the numbers define the ratio of $I_{Glu}/I_{Ap}$, and where peroxide response was measured at 0.65 V vs. a AgCl/Ag reference electrode.

The goal of the present invention is to provide more stable electropolymerized films, so that the biosensor performance is limited by the lifetime of the enzyme, not by the stability of the polymer film. It was found that the permselective behavior of the applied films was greatly influenced by the monomers employed and electropolymerization conditions. Thicker films tend to exclude interferences, but also have lower sensitivity to the analyte and increased response time. Polyphenol films were found to be very selective against acetaminophen and also stable long-term when considering the balance of selectivity and sensitivity. FIG. 14 shows the sensor response to 5 mM glucose as a function of the electrodeposition potential of the enzyme. At 1.3 V, the ratio of the response $I_{Glu}/I_{AP}$ is 276 (where $I_{Glu}$ and $I_{AP}$ are the current responses to glucose and acetaminophen respectively), largely due to the high enzyme activity resulting from the electrodeposition. The exclusion of AP therefore does not depend strongly on the deposition conditions for the enzyme. These results were obtained on sensors without the PU membrane, which reduces the response to glucose by a factor of less than 10 without significantly affecting the AP response. Accordingly, it was determined that the selectivity for the complete sensor should preferably be at least 28:1.

It was observed that modification of a Pt electrode by polyphenol or polyphenol and then 3-ATS films resulted in a loss of sensitivity for hydrogen peroxide by factors of 6.7 and 8.2 respectively (Table 2). However, a much greater decrease was observed for interferants such as acetaminophen, ascorbic acid and uric acid. Furthermore, the electrode modified with polyphenol/3-ATS was more selective than electrodes modified with only polyphenol, especially against acetaminophen. It was assumed that the small faradaic current from interferences occurs either by long-range slow electron transfer across the membrane or by electron transfer at a few microscopic defect sites in the membrane.

TABLE 2

Selectivities of Pt electrodes[a] modified with polyphenol (PPH) and (3-aminopropyl)trimethoxysilane (3-ATS)

| Analyte (0.1 mM) | Resp. at bare Pt (nA) (A) | Resp. at Pt/PPH (nA) (B) | Resp. at Pt/PPH/ATS (nA) (C) | Ratio A/B | Ratio A/C | Selectivity B[b] | Selectivity C[b] |
|---|---|---|---|---|---|---|---|
| $H_2O_2$ | 475 ± 32 | 71 ± 4 | 58 ± 4 | 6.71 | 8.2 | 1 | 1 |
| acetaminophen | 185 ± 14 | 0.16 ± 0.03 | 0.05 ± 0.002 | 1154 | 3692 | 172 | 449 |
| ascorbic acid | 154 ± 14 | 0.17 ± 0.02 | 0.09 ± 0.01 | 906 | 1711 | 135 | 208 |
| uric acid | 128 ± 11 | 0.18 ± 0.02 | 0.10 ± 0.01 | 710 | 1278 | 106 | 155 |

[a]A potential of 0.65 V vs. AgCl/Ag was applied to the Pt electrodes (n = 5) in pH 7.4 PBS solution at room temperature.
[b]Selectivity of hydrogen peroxide over interferants. There is no enzyme applied to the electrodes.

Stability of GOx Electrodes

Figure 15:
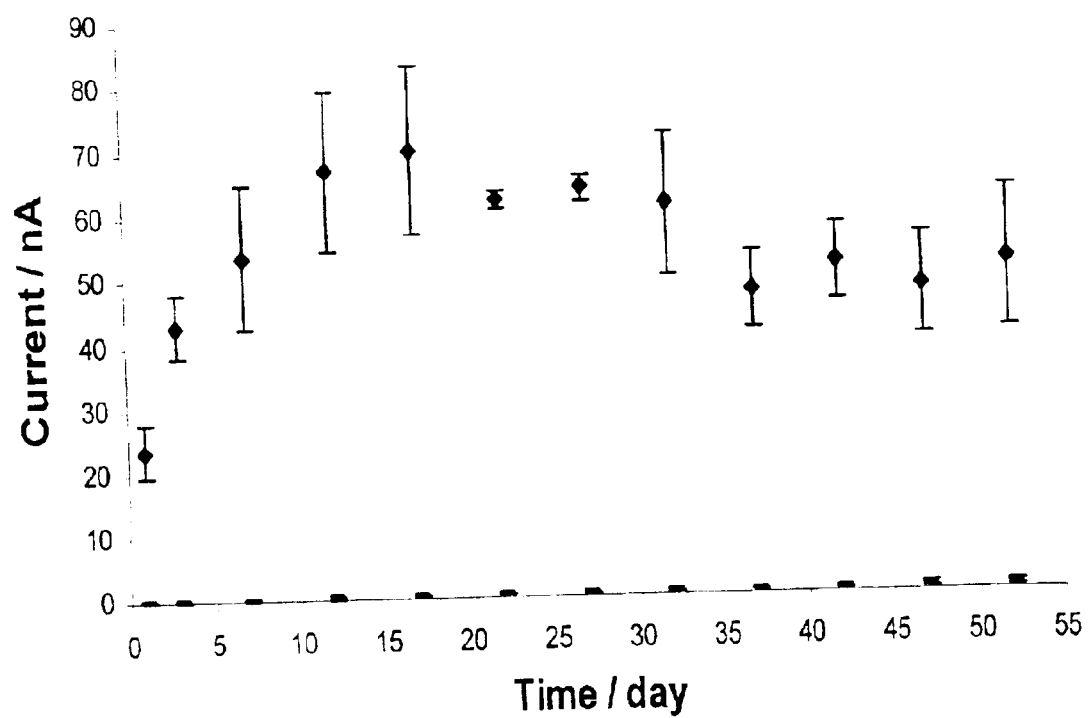
FIG. 15 is a graph depicting the stability of GOx electrodes (n=5) without the outer membrane, where the (♦) data points represent the response to 5 mM glucose and the (−) data points represent the response to 0.1 mM AP.

FIG. 15 illustrates the response of sensors to glucose and acetaminophen over a period of over 50 days. These sensors have no mass transfer-limiting PU membrane and therefore are a somewhat more accurate reflection of how the enzyme activity varies with time. These sensors do possess the 3-ATS film. The response increases initially, then reaches a somewhat lower and relatively constant value. The response to acetaminophen increases slightly over this period of time. The electropolymerization mechanism of phenol is based on simple radical initiation (Bartlett, P. N.; et al., *J. Electroanal. Chem.* 1993, 362, 1–12). It has previously been reported that polyhydroxyl compounds tended to stabilize the activity of the enzyme (Dong, S., et al.; *Anal. Chem.* 1994, 66, 3895–3899; Gilson, T. D.; et al., *In Biosensors and Chemical Sensors*; Edelman, P. G.; Wang, J., Eds.; ACS Symposium Series 487; American Chemical Society: Washington, D.C., 1992; Chapter 5[30]), a possible contributing factor to improved performance.

The presence of the 3-ATS film resulted in a significant improvement in the stability of the polyphenol film. The effectiveness of the 3-ATS deposit was significantly enhanced if a potential of 0.6 V was applied compared with no potential applied (data not shown). The fact that enhancement is specifically linked to an electrochemical reaction suggests that intermediates produced by phenol oxidation may play an important role. At the specified applied potential, the 3-ATS cannot be oxidized. As Table 2 also indicates, the presence of the 3-ATS film significantly improves the permselectivity of the polyphenol. When N-propyltrimethoxysilane was substituted for 3-ATS, the enhancement of permselectivity and stability are significantly reduced. Thus although it appears to be important to form a network by cross-linking of the silane function to form an Si—O—Si network, the reaction of the silane-amine function may be important. Oxidation of phenols can result in the production of quinoid structures, and the reaction of primary amines with them via Michael addition is well known. Indeed, the formation of quinoid structures will result not only in the reaction of the silane with oxidized forms of phenol, but the reaction of protein primary amines is also possible.

AFM measurements of the electrodeposited enzyme layer before and after electropolymerization show no apparent increase in the thickness of the enzyme layer (480 nm). This suggests that the polymer layer is not thicker than the enzyme layer and can form around and intermingle with the enzyme molecules.

Figure 16:
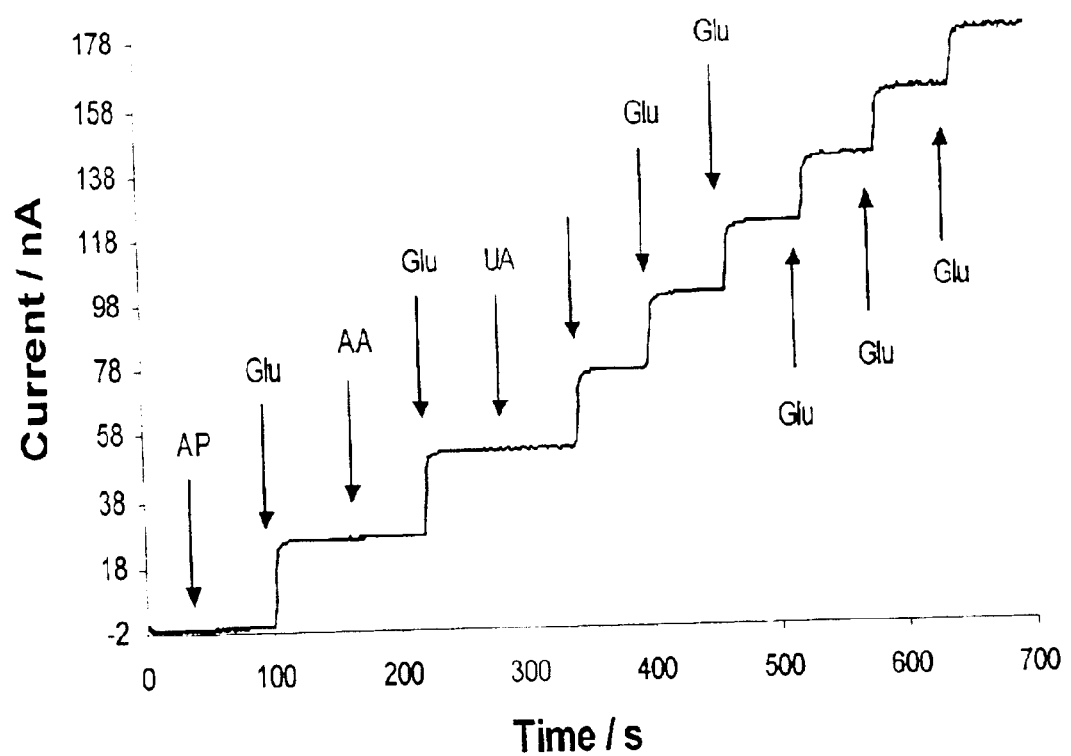
FIG. 16 is a current-time curve for a GOx electrode with outer membrane upon sequential addition of AP, glucose, AA and UA.

Performance of the Glucose Biosensor with a Mass Transfer-Limiting Outer Membrane FIG. 16 illustrates a typical current-time curve for the biosensor with PU outer membrane upon the injection of glucose and various electroactive interferences. The response to 0.1 mM AA, UA, and AP were essentially negligible. The response of electrodes to AA and UA were lower than AP, which corresponded to the well-known fact that AP is the most serious electrochemical interference so far encountered in the course of sensor development. There is some deterioration of the permselectivity with the complete sensor compared to the electropolymerized layer only. There are believed to be two reasons for this: 1. In the complete sensor the enzyme is buried within and intermingled with the permselective layer, as opposed to being on top of it and 2. There is a slight disruption of the inner membrane due to the solvent (THF and DMF) used to deposit the external membrane.

Figure 17:
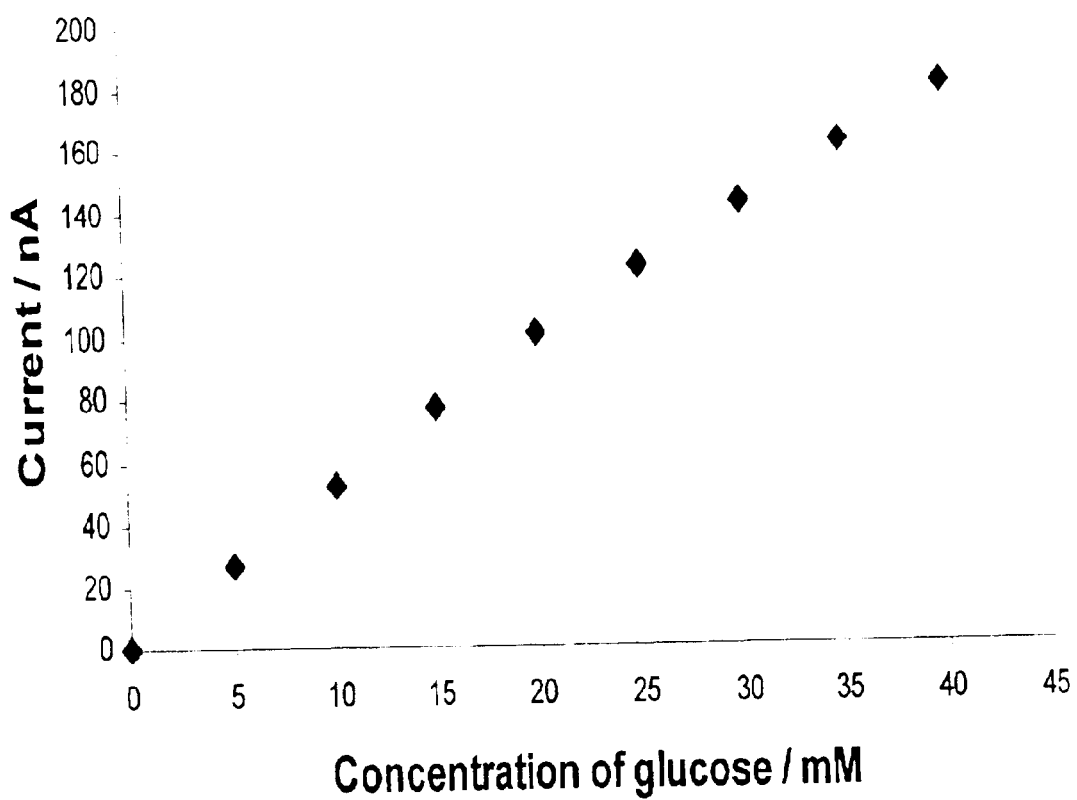
FIG. 17 is a calibration curve for the GOx electrode response to glucose in pH 7.4 PBS, where the applied potential was 650 mV (vs. AgCl/Ag (3M KCl))

The biosensor of this example demonstrated a 90% response to glucose within less than 4 s. This behavior stems from the fact that the growth of the non-conducting polyphenol film was largely self-limiting and the resulting deposit very thin (usually 10–100 nm). There is also no evidence of regular surface orientation of enzyme in the sensor of this example, but electrodeposition does seem to yield somewhat smoother deposits compared to simple adsorption. The thin polyphenol film also containing the enzyme has another advantage: the closer the enzyme molecules are to the electrode, the more hydrogen peroxide is collected and oxidized to regenerate oxygen. Elevated levels of oxygen in the enzyme layer lead to improved sensor linearity. This is illustrated in FIG. 17 where good linearity is observed up to over 20 mM.

Figure 18:
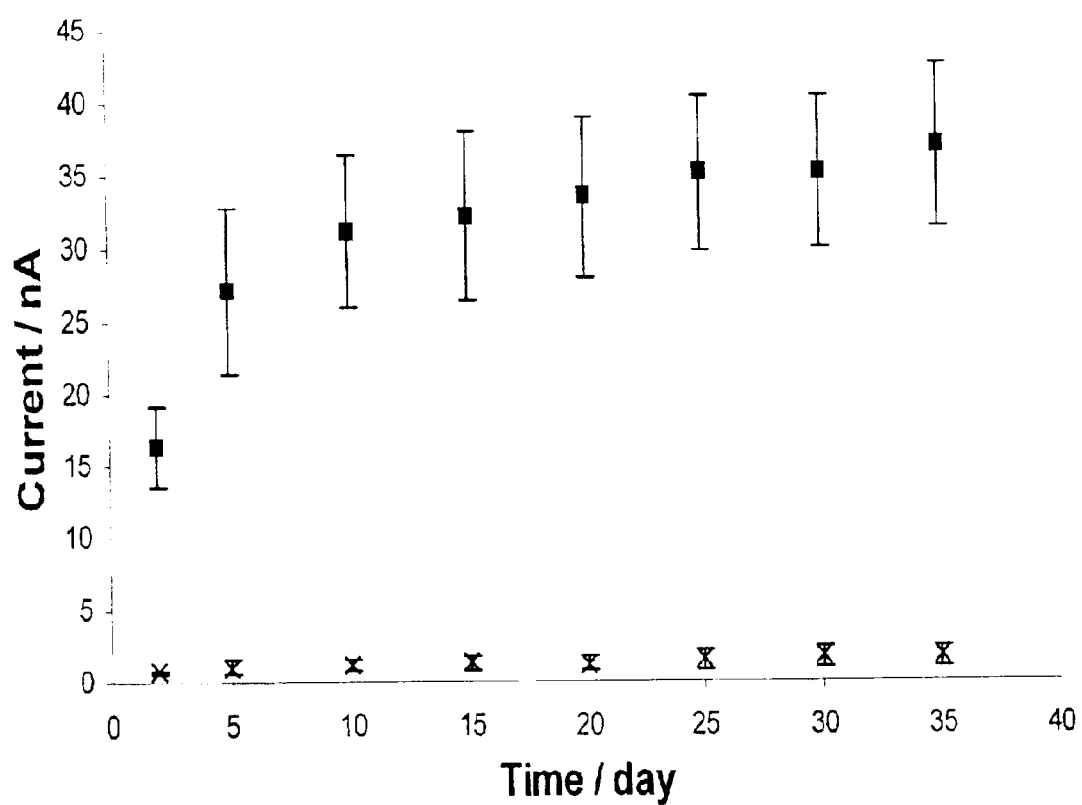
FIG. 18 is a graph of current vs. time demonstrating the long term stability of the preferred GOx electrode (n=8) having a PU outer membrane with the test conditions same as those set forth in the description of FIG. 17, with the (■) data points reflecting the response to 5 mM glucose and the (x) data points representing the response to 0.1 mM AP.

The stability of the complete biosensor was also investigated. Over a period of 35 days the response of the sensors to glucose (5 mM) and acetaminophen (0.1 mM) was checked periodically and the sensor stored in the interim in pH 7.4 phosphate buffer at 4° C. The results are shown in FIG. 18. Over a period of about 5 days the sensitivity of the sensors increased, after which they reached a stable value. There is a slight increase in the response to AP, but this is essentially compensated for by the increase in glucose response. The sensitivity and selectivity were stable even after over 6 months. The response data at Day 200 showed sensitivities of about 8.5 nA/mM to glucose and the response to 0.1 mM AP (the values for AA and UA of the same concentration were even smaller) was only 4.2% of that due to 5 mM glucose, the same as the mean value for the first 35 days.

The glucose sensors of the invention thus have a very high selectivity stability. As used herein, "selectivity stability" is measured by placing a glucose sensor in a 10 mL beaker equipped with a stirring bar and containing 5 mL of pH 7.4 phosphate buffered saline (phosphate buffer 0.1M, containing 0.15M NaCl) at room temperature. First a potential of 0.65 V is applied between the sensor sensing element and a AgCl/Ag reference electrode to establish a background current while maintaining stirring. After the current becomes stable (usually in about 0.5 h), a glucose solution is injected to give a final concentration of 0.5 mM glucose in the buffer solution. After a short time (40–60 seconds) a plateau in the recorded current-time curve is achieved, indicating that the sensor has reached its maximum response for that glucose concentration. The difference between the background current and maximum current is referred to as the current response to glucose ($I_{Glu}$). Acetaminophen (which interferes electrochemically with the detection of glucose) is then added at a concentration of 0.1 mM and the current is then registered after a plateau is reached (which may take up to 0.5 h). The current change resulting from the addition of the acetaminophen is defined as $I_{Inter}$. The selectivity value is defined as the percent change in the signal at 5 mM glucose according to the relationship % Interf=$(I_{Inter}/I_{Glu})\times 100$ (where $I_{Inter}=I_{Tot}-I_{Glu}$). Preferably, sensors in accordance with the invention have a selectivity stability which corresponds to a difference in selectivity values that varies no more than ±10% relative to the initial selectivity of the sensor for a period of at least 60 days, more preferably at least 100 days, and most preferably at least 180 days. In the sensor described in this example, the initial selectivity was 4.1%, and even at 200 days storage time, the selectivity was within the desired ±10% range (i.e., from 3.1 to 5.3%).

The overall performance of these sensors was compared with previously reported electropolymerization protocols as shown in Table 3. The linearity range and sensitivity are superior to sensors previously reported and response time is similarly quite short. Polypyrrole is a frequent choice for sensor construction (Guerrieri, A., et al.; Biosens. Bioelectron. 1998, 13, 103–112). However, many electropolymerized films including polypyrrole show excellent selectivity for the first several days of operation, after which the selectivity deteriorates rapidly. By contrast, the sensor of this example showed no change in either sensitivity or selectivity between 35 and 200 days

TABLE 3

Comparison of GOx electrodes prepared with different electropolymerized films

| Types of GOx electrode | Detection potential (mV) | Sensitivity nA/(mM × mm$^2$) | $T_{90}$ (s) | Linearity range (mM) | Reference |
|---|---|---|---|---|---|
| Pt/GOx/PPH/PATS/PU* | 650[a] | 1205 ± 217 | 4 | 25 | Preferred Electrode |
| Pt/RH-GOx/PC | 400[b] | ~800 | | 15 | [15] |
| Pt/PMPS/GOx(BSA/GA)/PU | 600[a] | 42 | 60 | 15 | [22] |

TABLE 3-continued

Comparison of GOx electrodes prepared with different electropolymerized films

| Types of GOx electrode | Detection potential (mV) | Sensitivity nA/(mM × mm$^2$) | T$_{90}$ (s) | Linearity range (mM) | Reference |
|---|---|---|---|---|---|
| Pt/PPy$_{ox}$/GOx(BSA/GA) | 700$^a$ | 1189 | 1.2 | 12 | [33] |
| Pt/PPy-GOx | 700$^a$ | 283 | | 6 | [34] |
| Pt/PPy-GOx/oPPD | 700$^a$ | 283 | | 6 | [35] |

*n = 8
PPH: polyphenol
PATS: poly((3-aminopropyl)trimethoxysilane)
PU: polyurethane
PMPS: poly((3-mercaptopropyl)trimethoxysilane)
BSA: bovine serum albumin
GA: glutaraldehyde
PPY: polypyrrole
PPy$_{ox}$: overoxidized polypyrrole
RH: redox hydrogel
PC: polycarbonate
oPPD: poly(o-phenylenediamine)
T$_{90}$: response time which is defined as the time needed to reach 90% of the maximum response;
$^a$vs. AgCl/Ag
$^b$vs. SCE The superior sensor performance of the sensor of this example is attributed in part to the presence of a thin membrane serving the dual purpose of stabilizing the immobilized enzyme and providing a stable permselective layer for elimination of electroactive interferences. High sensitivity can be achieved because the enzyme is deposited first, thus creating a compact layer. The presence of the enzyme does not interfere significantly with the creation of a polymer layer largely lacking in defects.

We claim:

1. In a method of depositing an enzyme onto an electrically conductive substrate wherein the substrate and a reference electrode are immersed in an aqueous conductive dispersion containing said enzyme and a potential is applied across the substrate and reference electrode to cause the enzyme to accumulate on the substrate, the improvement which comprises the step of adding to said aqueous dispersion a surfactant in an amount at least about equal to the critical micelle concentration for the surfactant in the dispersion.

2. The method of claim 1, said conductive substrate being a biosensor electrode.

3. The method of claim 2, said biosensor electrode including a noble metal therein.

4. The method of claim 2, said biosensor electrode formed of Pt-Ir wire.

5. The method of claim 1, said enzyme selected from the group consisting of the oxidase enzymes.

6. The method of claim 5, said enzyme selected from the group consisting of the glucose, lactate, glutamate, pyruvate, cholesterol, and choline oxidase enzymes.

7. The method of claim 1, said enzyme being glucose oxidase.

8. The method of claim 1, said potential being in the range of from about 1.1 to 1.4 volts versus the other electrode.

9. The method of claim 1, said surfactant being a nonionic surfactant.

10. The method of claim 9, said surfactant comprising octylphenol polymerized with ethylene oxide.

11. The method of claim 10, said surfactant comprising between about 9–10 moles of ethylene oxide per mole of octylphenol.

12. The method of claim 1, said aqueous dispersion comprising a phosphate buffered saline solution of pH about 7.

13. The method of claim 1, said surfactant composition being in the range of from about said critical micelle concentration up to about 10 times the critical micelle composition.

14. The method of claim 1, said potential being applied for a period of from about 40 to 80 minutes.

15. The method of claim 1, the molar ratio of said enzyme to said surfactant in said dispersion ranging from about 0.02 to 0.2.

16. The method of claim 1, said accumulated enzyme on said substrate having a thickness of from about 300 to 600 nm.

17. A method of preparing a biosensor comprising the steps of:
providing an electrically conductive biosensor electrode;
immersing said biosensor electrode and a reference electrode in an aqueous conductive dispersion containing an enzyme and a surfactant in an amount at least equal to the critical micelle concentration for the surfactant in the dispersion;
applying a potential across said biosensor electrode and said reference electrode to cause said enzyme to deposit on the biosensor electrode; and
immersing said enzyme-deposited biosensor electrode in a synthetic monomer, and electropolymerizing the monomer to create a polymer layer intermingled with said deposited enzyme.

18. The method of claim 17, said biosensor electrode including a noble metal therein.

19. The method of claim 18, said biosensor electrode formed of Pt-Ir wire.

20. The method of claim 17, said enzyme selected from the group consisting of oxidase enzymes.

21. The method of claim 20, said enzyme selected from the group consisting of the glucose, lactate, glutamate, pyruvate, cholesterol, and choline oxidase enzymes.

22. The method of claim 21, said enzyme being glucose oxidase.

23. The method of claim 17, said potential being in the range of from about 1.1 to 1.4 volts versus the other electrode.

24. The method of claim 17, said surfactant being a nonionic surfactant.

25. The method of claim 24, said surfactant comprising octylphenol polymerized with ethylene oxide.

26. The method of claim 25, said surfactant comprising between about 9–10 moles of ethylene oxide per mole of octylphenol.

27. The method of claim 17, said aqueous dispersion comprising a phosphate buffered saline solution of pH about 7.

28. The method of claim 17, said surfactant composition being in the range of from about said critical micelle concentration up to about 10 times the critical micelle composition.

29. The method of claim 17, said potential being applied for a period of from about 40 to 80.

30. The method of claim 17, the molar ratio of said enzyme to said surfactant in said dispersion ranging from about 0.02 to 0.2.

31. The method of claim 17, said deposited enzyme on said electrode having a thickness of from about 300 to 600 nm.

32. The method of claim 17, said polymer layer having a thickness of up to about 100 nm.

33. The method of claim 32, said polymer layer having a thickness of from about 10 to 100 nm.

34. The method of claim 17, said monomer being phenol or a substituted phenol.

35. The method of claim 17, including the step of applying a film of (3-aminopropyl) trimethoxysilane over said polymer layer.

36. The method of claim 35, including the step of applying a polyurethane coating over said film.

37. The method of claim 36, said coating having a thickness of from about 1 to 10 microns.

* * * * *